United States Patent
Mattar et al.

(10) Patent No.: US 8,109,152 B2
(45) Date of Patent: Feb. 7, 2012

(54) MULTIPHASE CORIOLIS FLOWMETER

(75) Inventors: Wade M. Mattar, Wrentham, MA (US); Manus P. Henry, Oxford (GB); Mihaela D. Duta, Oxford (GB); Michael S. Tombs, Oxford (GB)

(73) Assignee: Invensys Systems, Inc., Foxboro, MA (US)

( * ) Notice: Subject to any disclaimer, the term of this patent is extended or adjusted under 35 U.S.C. 154(b) by 0 days.

(21) Appl. No.: 12/788,994

(22) Filed: May 27, 2010

(65) Prior Publication Data

US 2011/0016984 A1    Jan. 27, 2011

Related U.S. Application Data

(63) Continuation of application No. 11/686,166, filed on Mar. 14, 2007, now Pat. No. 7,726,203, which is a continuation of application No. 11/344,140, filed on Feb. 1, 2006, now Pat. No. 7,207,229, which is a continuation of application No. 10/773,459, filed on Feb. 9, 2004, now Pat. No. 7,059,199.

(60) Provisional application No. 60/445,795, filed on Feb. 10, 2003, provisional application No. 60/452,934, filed on Mar. 10, 2003.

(51) Int. Cl.
*G01F 1/84* (2006.01)

(52) U.S. Cl. .................................. 73/861.355

(58) Field of Classification Search ............ 73/861.355, 73/861.356, 861.357
See application file for complete search history.

(56) References Cited

U.S. PATENT DOCUMENTS

| 5,804,742 | A | * | 9/1998 | Rademacher-Dubbick ................. 73/861.357 |
| 2011/0016988 | A1 | * | 1/2011 | Tombs et al. |

* cited by examiner

*Primary Examiner* — Jewel V Thompson

(57) ABSTRACT

A flowmeter is disclosed. The flowmeter includes a vibratable flowtube, and a driver connected to the flowtube that is operable to impart motion to the flowtube. A sensor is connected to the flowtube and is operable to sense the motion of the flowtube and generate a sensor signal. A controller is connected to receive the sensor signal. The controller is operable to determine a first flow rate of a first phase within a two-phase flow through the flowtube and determine a second flow rate of a second phase within the two-phase flow.

24 Claims, 20 Drawing Sheets

MULTIPHASE CORIOLIS FLOWMETER

CROSS-REFERENCE TO RELATED APPLICATIONS

This application is a continuation of U.S. application Ser. No. 11/686,166 filed Mar. 14, 2007, issuing as U.S. Pat. No. 7,726,203 on Jun. 1, 2010 and titled "MULTIPHASE CORIOLIS FLOWMETER," which is a continuation of U.S. application Ser. No. 11/344,140, filed Feb. 1, 2006, now U.S. Pat. No. 7,207,229 issued on Apr. 24, 2007 and titled "MULTIPHASE CORIOLIS FLOWMETER," which is a continuation of U.S. application Ser. No. 10/773,459, filed Feb. 9, 2004, now U.S. Pat. No. 7,059,199 issued on Jun. 13, 2006 and titled "MULTIPHASE CORIOLIS FLOWMETER," which claims priority under 35 USC §119(e) to U.S. Patent Application Ser. No. 60/445,795, filed on Feb. 10, 2003, and titled MULTIPHASE CORIOLIS FLOWMETER. This application also claims priority to U.S. Application Ser. No. 60/452,934, filed on Mar. 10, 2003, now expired and titled MULTIPHASE CORIOLIS FLOWMETER. These applications are hereby incorporated by reference.

TECHNICAL FIELD

This description relates to flowmeters.

BACKGROUND

Flowmeters provide information about materials being transferred through a conduit, or flowtube. For example, mass flowmeters provide an indication of the mass of material being transferred through a conduit. Similarly, density flowmeters, or densitometers, provide an indication of the density of material flowing through a conduit. Mass flowmeters also may provide an indication of the density of the material, and therefore an indication of the volumetric flow rate.

For example, Coriolis-type mass flowmeters are based on the Coriolis effect, in which material flowing through a conduit becomes a radially-travelling mass that is affected by a Coriolis force and therefore experiences an acceleration. Many Coriolis-type mass flowmeters induce a Coriolis force by sinusoidally oscillating a conduit about a pivot axis orthogonal to the length of the conduit. In such mass flowmeters, the Coriolis reaction force experienced by the traveling fluid mass is transferred to the conduit itself and is manifested as a deflection or offset of the conduit in the direction of the Coriolis force vector in the plane of rotation.

SUMMARY

According to one general aspect, a flowmeter includes a vibratable flowtube, a driver connected to the flowtube and operable to impart motion to the flowtube, a sensor connected to the flowtube and operable to sense the motion of the flowtube and generate a sensor signal, and a controller connected to receive the sensor signal, the controller being operable to determine a first flow rate of a first phase within a two-phase flow through the flowtube and determine a second flow rate of a second phase within the two-phase flow.

Implementations may include one or more of the following features. For example, the first phase may include a gas and the second phase may include a liquid.

The controller may be operable to input an apparent density of the two-phase flow detected by the flowmeter and output a corrected density of the two-phase flow. The controller may be operable to correct the apparent density based on a theoretical relationship between the apparent density and the corrected density, or based on an empirical relationship between the apparent density and the corrected density (such as, for example, a table storing relationships between the apparent density and the corrected density).

The controller may be operable to input an apparent mass flow rate of the two-phase flow detected by the flowmeter and output a corrected mass flow rate of the two-phase flow. The controller may be operable to correct the apparent mass flow rate based on a theoretical or empirical relationship, such as a tabular relationship, between the apparent mass flow rate and the corrected mass flow rate.

The controller may be operable to input an apparent first phase fraction of the two-phase flow detected by the flowmeter that defines an amount of the first phase in the two-phase flow and output a corrected first phase fraction of the two-phase flow. The controller may be operable to input a first phase fraction of the two-phase flow detected by a phase fraction sensor that is external to the flowmeter.

The controller may be operable to determine the first flow rate and the second flow rate based on corrected values for a detected density and detected mass flow rate of the two-phase flow. The controller may be operable to determine the first flow rate and the second flow rate based on a corrected value for a detected first phase fraction that defines an amount of the first phase in the two-phase flow. The controller may be operable to determine the first flow rate and the second flow rate based on densities of the first phase and the second phase, respectively.

The controller may be operable to determine a first superficial velocity of the first phase and a second superficial velocity of the second phase, based on the first flow rate and the second flow rate, respectively. The controller may be operable to determine a flow regime of the two-phase flow, based on the first superficial velocity and the second superficial velocity. The controller may be operable to determine a slip velocity between the first phase and the second phase, based on an average velocity of the first phase and an average velocity of the second phase. The controller may be operable to provide corrections to the first flow rate and the second flow rate, based on the first and second superficial velocities, the determined flow regime, or the slip velocity, to thereby obtain a corrected first flow rate and a corrected second flow rate.

According to another general aspect, a method includes determining a bulk density of a two-phase flow through a flowtube, the two-phase flow including a first phase and a second phase, determining a bulk mass flow rate of the two-phase flow, and determining a first mass flow rate of the first phase, based on the bulk density and the bulk mass flow rate.

Implementations may include one or more of the following features. For example, a second mass flow rate of the second phase may be determined, based on the bulk density and the bulk mass flow rate. In determining the bulk density, an apparent bulk density of the two-phase flow may be determined, and the apparent bulk density may be corrected to obtain the bulk density.

In correcting the apparent bulk density, the apparent bulk density may be input into a theoretical relationship that relates the apparent bulk density to a corrected bulk density, or may be input into an empirical relationship that relates the apparent bulk density to a corrected bulk density.

In correcting the apparent bulk density, a first density of the first phase may be input. A first phase fraction of the two-phase flow may be determined, based on the bulk density, the first density of the first phase, and a second density of the second phase. In determining the first mass flow rate of the first phase, the first mass flow rate may be determined based on the first phase fraction and the first density.

A first superficial velocity of the first phase and a second superficial velocity of the second phase may be determined, based on the first mass flow rate and the second mass flow rate, respectively. A flow regime of the two-phase flow may be determined, based on the first superficial velocity and the second superficial velocity. A slip velocity between the first phase and the second phase may be determined, based on an average velocity of the first phase and an average velocity of the second phase. Corrections may be provided to the first flow rate and the second flow rate, based on the first and second superficial velocities, the determined flow regime, or the slip velocity.

The first phase may include a gas and the second phase may include a liquid.

According to another general aspect, a flowmeter controller includes a density correction system operable to input an apparent density of a two-phase flow and output a corrected density of the two-phase flow, the two-phase flow including a first phase and a second phase, a mass flow rate correction system operable to input an apparent mass flow rate of the two-phase flow and output a corrected mass flow rate of the two-phase flow, and a flow component mass flow rate determination system operable to determine a first mass flow rate of the first phase, based on the corrected density and the corrected mass flow rate.

Implementations may include one or more of the following features. For example, the flow component mass flow rate determination system may be operable to determine a second mass flow rate of the second phase, based on the corrected density and the corrected mass flow.

The first phase may include a liquid and the second phase may include a gas. A phase fraction determination system may be included that is operable to determine a corrected phase fraction of the two-phase flow, wherein the flow component mass flow rate determination system may be operable to determine the first flow rate and the second flow rate based on the corrected phase fraction. The phase fraction determination system may be a void fraction determination system that determines an amount of the gas in the two-phase flow.

A superficial velocity determination system may be included that is operable to determine a first superficial velocity of the first phase and a second superficial velocity of the second phase. The flowmeter controller may include a flow regime determination system operable to determine a flow regime of the two-phase flow.

The flow regime determination system may be further operable to determine a phase slip velocity with respect to an average velocity of the first phase and an average velocity of the second phase. The flow component mass flow rate determination system may be operable to improve the determination of the first mass flow rate and the second mass flow rate, based on the first and second superficial velocities, the flow regime, or the phase slip velocity.

The details of one or more implementations are set forth in the accompanying drawings and the description below. Other features will be apparent from the description and drawings, and from the claims.

DETAILED DESCRIPTION

Types of flowmeters include digital flowmeters. For example, U.S. Pat. No. 6,311,136, which is hereby incorporated by reference, discloses the use of a digital flowmeter and related technology including signal processing and measurement techniques. Such digital flowmeters may be very precise in their measurements, with little or negligible noise, and may be capable of enabling a wide range of positive and negative gains at the driver circuitry for driving the conduit. Such digital flowmeters are thus advantageous in a variety of settings. For example, commonly-assigned U.S. Pat. No. 6,505,519, which is incorporated by reference, discloses the use of a wide gain range, and/or the use of negative gain, to prevent stalling and to more accurately exercise control of the flowtube, even during difficult conditions such as two-phase flow (e.g., a flow containing a mixture of liquid and gas).

Although digital flowmeters are specifically discussed below with respect to, for example, FIGS. 1 and 2, it should be understood that analog flowmeters also exist. Although such analog flowmeters may be prone to typical shortcomings of analog circuitry, e.g., low precision and high noise measurements relative to digital flowmeters, they also may be compatible with the various techniques and implementations discussed herein. Thus, in the following discussion, the term "flowmeter" or "meter" is used to refer to any type of device and/or system in which a Coriolis flowmeter system uses various control systems and related elements to measure a mass flow, density, and/or other parameters of a material(s) moving through a flowtube or other conduit.

Figure 1A:
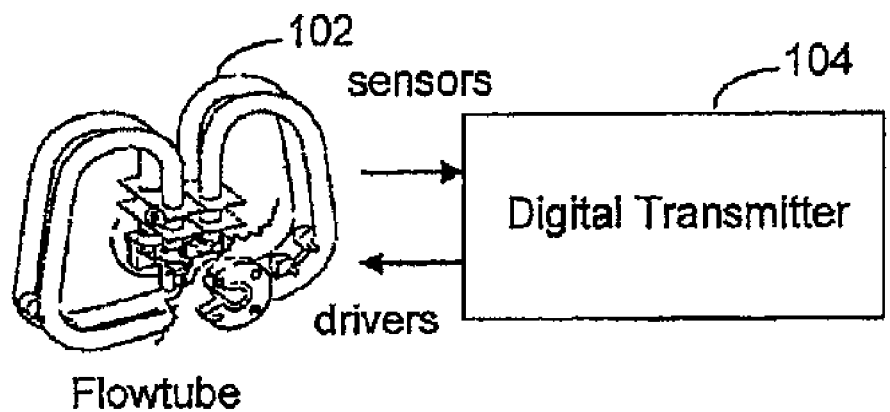
FIG. 1A is an illustration of a Coriolis flowmeter using a bent flowtube.

FIG. 1A is an illustration of a digital flowmeter using a bent flowtube 102. Specifically, the bent flowtube 102 may be used to measure one or more physical characteristics of, for example, a (traveling) fluid, as referred to above. In FIG. 1A, a digital transmitter 104 exchanges sensor and drive signals with the bent flowtube 102, so as to both sense an oscillation of the bent flowtube 102, and to drive the oscillation of the bent flowtube 102 accordingly. By quickly and accurately determining the sensor and drive signals, the digital transmitter 104, as referred to above, provides for fast and accurate operation of the bent flowtube 102. Examples of the digital transmitter 104 being used with a bent flowtube are provided in, for example, commonly-assigned U.S. Pat. No. 6,311,136.

Figure 1B:
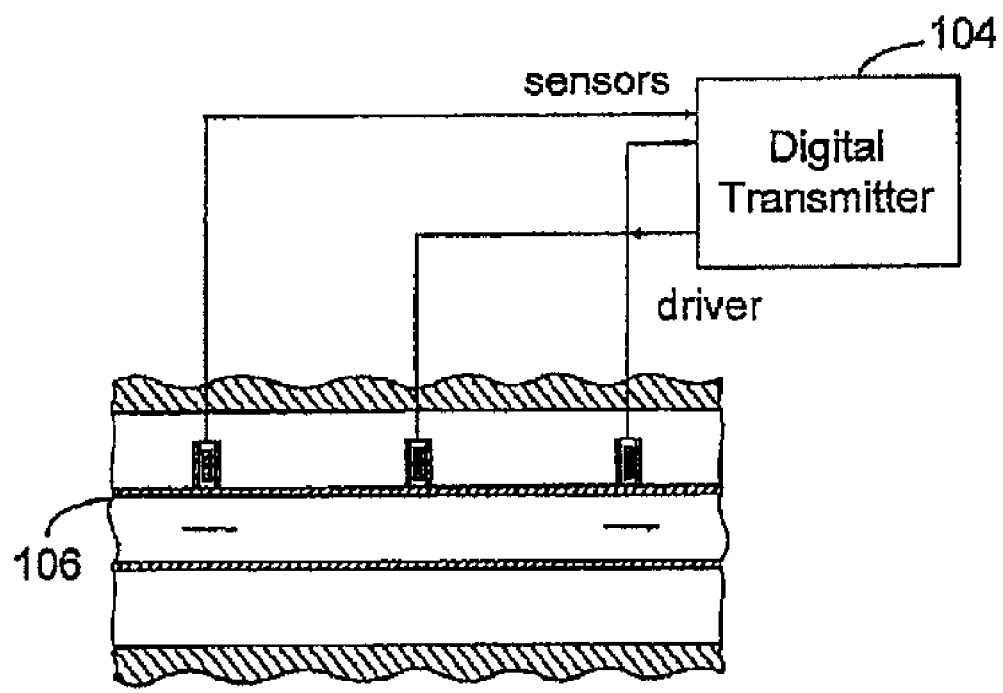
FIG. 1B is an illustration of a Coriolis flowmeter using a straight flowtube.

FIG. 1B is an illustration of a digital flowmeter using a straight flowtube 106. More specifically, in FIG. 1B, the straight flowtube 106 interacts with the digital transmitter 104. Such a straight flowtube operates similarly to the bent flowtube 102 on a conceptual level, and has various advantages/disadvantages relative to the bent flowtube 102. For example, the straight flowtube 106 may be easier to (completely) fill and empty than the bent flowtube 102, simply due to the geometry of its construction. In operation, the bent flowtube 102 may operate at a frequency of, for example, 50-110 Hz, while the straight flowtube 106 may operate at a frequency of, for example, 300-1,000 Hz. The bent flowtube 102 represents flowtubes having a variety of diameters, and may be operated in multiple orientations, such as, for example, in a vertical or horizontal orientation.

Figure 2:
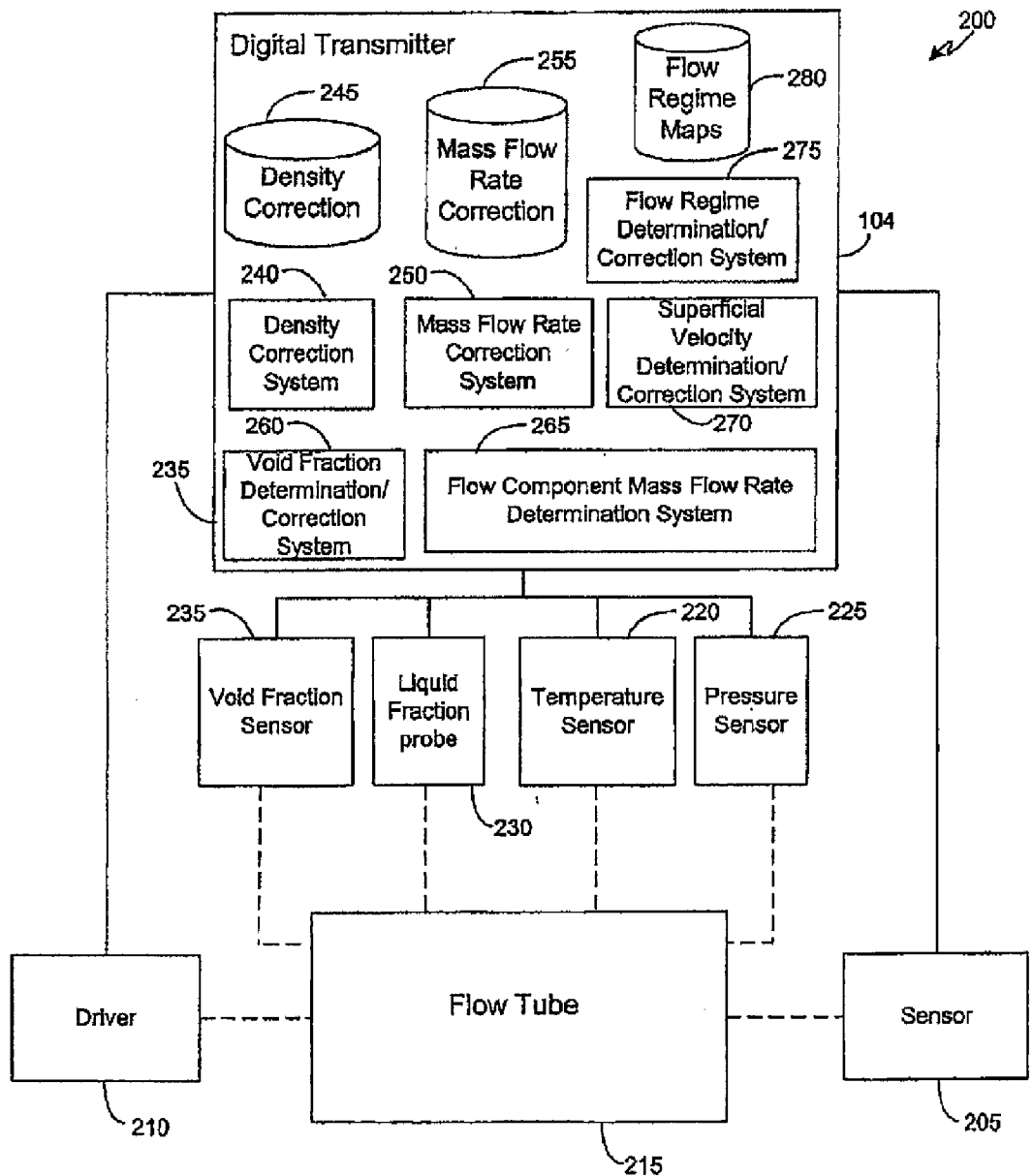
FIG. 2 is a block diagram of a Coriolis flowmeter.

Referring to FIG. 2, a digital mass flowmeter 200 includes the digital transmitter 104, one or more motion sensors 205, one or more drivers 210, a flowtube 215 (which also may be referred to as a conduit, and which may represent either the bent flowtube 102, the straight flowtube 106, or some other type of flowtube), and a temperature sensor 220. The digital transmitter 104 may be implemented using one or more of, for example, a processor, a Digital Signal Processor (DSP), a field-programmable gate array (FPGA), an ASIC, other programmable logic or gate arrays, or programmable logic with a processor core. It should be understood that, as described in U.S. Pat. No. 6,311,136, associated digital-to-analog converters may be included for operation of the drivers 210, while analog-to-digital converters may be used to convert sensor signals from the sensors 205 for use by the digital transmitter 104.

The digital transmitter 104 generates a measurement of, for example, density and/or mass flow of a material flowing through the flowtube 215, based at least on signals received from the motion sensors 205. The digital transmitter 104 also controls the drivers 210 to induce motion in the flowtube 215. This motion is sensed by the motion sensors 205.

Density measurements of the material flowing through the flowtube are related to, for example, the frequency of the motion of the flowtube 215 that is induced in the flowtube 215 by a driving force supplied by the drivers 210, and/or to the temperature of the flowtube 215. Similarly, mass flow through the flowtube 215 is related to the phase and frequency of the motion of the flowtube 215, as well as to the temperature of the flowtube 215.

The temperature in the flowtube 215, which is measured using the temperature sensor 220, affects certain properties of the flowtube, such as its stiffness and dimensions. The digital transmitter 104 may compensate for these temperature effects. Also in FIG. 2, a pressure sensor 225 is in communication with the transmitter 104, and is connected to the flowtube 215 so as to be operable to sense a pressure of a material flowing through the flowtube 215.

It should be understood that both the pressure of the fluid entering the flowtube 215 and the pressure drop across relevant points on the flowtube may be indicators of certain flow conditions. Also, while external temperature sensors may be used to measure the fluid temperature, such sensors may be used in addition to an internal flowmeter sensor designed to measure a representative temperature for flowtube calibrations. Also, some flowtubes use multiple temperature sensors for the purpose of correcting measurements for an effect of differential temperature between the process fluid and the environment (e.g., a case temperature of a housing of the flowtube). As discussed in more detail below, one potential use for the inlet fluid temperature and pressure measurements is to calculate the actual densities of a liquid and gas in a two-phase flow, based on predefined formulae.

A liquid fraction probe 230 refers to a device for measuring a volume fraction of liquid, e.g., water, when a liquid in the flowtube 215 includes water and another fluid, such as oil. Of course, such a probe, or similar probes, may be used to measure the volume fraction of a fluid other than water, if such a measurement is preferred or if the liquid does not include water. In the below description, a measured liquid is generally assumed to be water for the purposes of example, so that the liquid fraction probe 230 is generally referred to as a water fraction probe 230, or a water-cut probe 230.

A void fraction sensor 235 measures a percentage of a material in the flowtube 215 that is in gaseous form. For example, water flowing through the flowtube 215 may contain air, perhaps in the form of bubbles. Such a condition, in which the material flowing through the flowtube 215 contains more than one material is generally referred to as "two-phase flow." In particular, the term "two-phase flow" may refer to a liquid and a gas; however, "two-phase flow" also may refer to other combinations of materials, such as two liquids (e.g., oil and water).

Various techniques, represented generally in FIG. 2 by the void fraction sensor 235, exist for measuring the gas void fraction in a two-phase flow of liquid and gas. For example, various sensors or probes exist that may be inserted into the flow to determine a gas void fraction. As another example, a venturi tube (i.e., a tube with a constricted throat that determines fluid pressures and velocities by measurement of differential pressures generated at the throat as a fluid traverses the tube), relying on the fact that gas generally moves with a higher velocity than liquid(s) through a restriction, may be used to determine a pressure gradient and thereby allow a determination of the gas void fraction. Measurements of gas void fractions also may be obtained using equipment that is wholly external to the flowtube. For example, sonar measurements may be taken to determine gas void fraction. As a specific example of such a sonar-based system, the SONARtrac™ gas void fraction monitoring system produced by CiDRA Corporation of Wallingford, Conn. may be used.

In this description, an amount of gas in a flowing fluid, measured by the void fraction sensor or otherwise determined, is referred to as void fraction or $\alpha$, and is defined as $\alpha$=volume of gas/total volume=volume of gas/(volume of liquid+volume of gas). Accordingly, a quantity referred to herein as the liquid fraction is defined as $1-\alpha$.

In many applications where mass flow measurements are required, the void fraction of the flow can be as high as 20, 30, 40% or more. However, even at very small void fractions of 0.5%, the fundamental theory behind the coriolis flowmeter becomes less applicable.

Moreover, a presence of gas in the fluid flow also may affect a measurement of a density of the fluid flow, generally causing the density measurement to read lower. That is, it should be understood that a density $\rho_{liquid}$ of a liquid flowing by itself through a flowtube will be higher than an actual density $\rho_{true}$ of a two-phase flow containing the liquid and a gas, since a density of the gas (e.g., air) will generally be lower than a density of the liquid (e.g., water) in the two-phase flow. In other words, there is a density reduction when gas is added to a liquid flow that previously contained only the liquid.

Beyond this physical phenomenon, a coriolis meter measuring a two-phase fluid flow containing gas may output a density reading $\rho_{apparent}$ that is an ostensible measurement of the bulk density of the two-phase flow (e.g., of the water and air combined). This raw measurement $\rho_{apparent}$ will generally be different (lower) than the actual bulk density $\rho_{true}$ of the two-phase flow. For example, the resonant frequency used by the flowmeter may be artificially high, due to relative motion of the gas in the fluid flow, which would cause the density measurement to read low. It should be understood that many conventional prior art flowmeters were unconcerned with this problem, since most such coriolis meters fail to continue operating (e.g. stall or output inaccurate measurements) at even the slightest amounts of void fraction.

U.S. Pat. No. 6,505,519, which is incorporated by reference above, discloses that such a variation of $\rho_{apparent}$ (i.e., an indicated raw or bulk density reading of a two-phase flow that is output by a coriolis flowmeter) from $\rho_{true}$ (i.e., an actual raw or bulk density of the two-phase flow) may be characterized by a variety of techniques. As a result, a measured $\rho_{apparent}$ may be corrected to obtain an actual bulk density $\rho_{corrected}$, which is, at least approximately, equal to $\rho_{true}$.

Somewhat similarly, an indicated raw or bulk mass flow rate $MF_{apparent}$ (i.e., a mass flow rate of the entire two-phase flow) measured by a coriolis flowmeter may be different by a predictable or characterizable amount from an actual bulk mass flow rate $MF_{true}$. It should be understood that correction techniques for corrected bulk mass flow rate $MF_{true}$ may be different than the techniques for correcting for density. For example, various techniques for correcting a measured $MF_{apparent}$ to obtain an actual $MF_{true}$ (or, at least, $MF_{corrected}$) are discussed in U.S. Pat. No. 6,505,519.

Examples of detailed techniques for correcting $\rho_{apparent}$ and $MF_{apparent}$ are discussed in more detail below. Generally speaking, though, with respect to FIG. 2, the digital transmitter is shown as including a density correction system 240, which has access to a density correction database 245, and a mass flow rate correction system 250, which has access to a mass flow correction database 255. As discussed in more detail below, the databases 245 and 255 may contain, for example, correction algorithms that have been derived theoretically or obtained empirically, and/or correction tables that provide corrected density or mass flow values for a given set of input parameters. The databases 245 and 255 also may store a variety of other types of information that may be useful in performing the density or mass flow corrections. For example, the density correction database may store a number of densities $\rho_{liquid}$ corresponding to particular liquids (e.g., water or oil).

Further in FIG. 2, a void fraction determination/correction system 260 is operable to determine a void fraction of a two-phase flow including a liquid and a gas. In one implementation, for example, the void fraction determination/correction system 260 may determine an actual void fraction $\alpha_{true}$ from the corrected density $\rho_{true}$. In another implementation, the void fraction determination/correction system 260 may input an apparent or indicated void fraction measurement obtained by the void fraction sensor 235, and may correct this measurement based on an error characterization similar to the density and mass flow techniques referred to above. In another implementation, the void fraction sensor 235 may be operable to directly measure an actual void fraction $\alpha_{true}$, in which case the void fraction determination/correction system 260 simply inputs this measurement.

Once the factors of $\rho_{true}$, $MF_{true}$, and $\alpha_{true}$ have been determined, and perhaps in conjunction with other known or discoverable quantities, a flow component mass flow rate determination system 265 operates to simultaneously determine a mass flow rate for the liquid phase component and a mass flow rate for the gas phase component. That is, the transmitter 104 is operable to determine individual flowrates $MF_{liquid}$ and $MF_{gas}$ of the flow components, as opposed to merely determining the bulk flowrate of the combined or total two-phase flow $MF_{true}$. Although, as just referred to, such measurements may be determined and/or output simultaneously, they also may be determined separately or independently of one another.

Once the component flow rates $MF_{liquid}$ and $MF_{gas}$ have been determined in the manner generally outlined above, these initial determinations may be improved upon by a process that relies on superficial velocities of the flow components, slip velocities between the components, and/or an identified flow regime of the flow. In this way, improved values for flow rates $MF_{liquid}$ and $MF_{gas}$ may be obtained, or may be obtained over time as those flow rates change.

Superficial velocities are referred to herein as those velocities that would exist if the same mass flow rate of a given phase was traveling as a single phase through the flowtube 215. A superficial velocity determination/correction system 270 is included in the transmitter 104 for, for example, determining an apparent or corrected superficial velocity of a gas or liquid in the two-phase flow.

Slip velocities refer to a condition in which gas and liquid phases in a two-phase flow have different average velocities. That is, an average velocity of a gas $AV_{gas}$ is different from an average velocity of a liquid $AV_{liquid}$. As such, a phase slip S may be defined as $S=AV_{gas}/AV_{liquid}$.

A flow regime is a term that refers to a characterization of the manner in which the two phases flow through the flowtube 215 with respect to one another and/or the flowtube 215, and may be expressed, at least partially, in terms of the superficial velocities just determined. For example, one flow regime is known as the "bubble regime," in which gas is entrained as bubbles within a liquid. As another example, the "slug regime" refers to a series of liquid "plugs" or "slugs" separated by relatively large gas pockets. For example, in vertical flow, the gas in a slug flow regime may occupy almost an entire cross-sectional area of the flowtube 215, so that the resulting flow alternates between high-liquid and high-gas composition. Other flow regimes are known to exist and to have certain defined characteristics, including, for example, the annular flow regime, the dispersed flow regime, and froth flow regime, and others.

The existence of a particular flow regime is known to be influenced by a variety of factors, including, for example, a gas void fraction in the fluid flow, an orientation of the flowtube 215 (e.g., vertical or horizontal), a diameter of the flowtube 215, the materials included within the two-phase flow, and the velocities (and relative velocities) of the materials within the two phase flow. Depending on these and other factors, a particular fluid flow may transition between several flow regimes over a given period of time.

Information about phase slip may be determined at least in part from flow regime knowledge. For example, in the bubble flow regime, assuming the bubbles are uniformly distributed, there may be little relative motion between the phases. Where the bubbles congregate and combine to form a less uniform distribution of the gas phase, some slippage may occur between the phases, with the gas tending to cut through the liquid phase.

In FIG. 2, a flow regime determination system 275 is included that has access to a database 280 of flow regime maps. In this way, information about an existing flow regime, including phase slip information, may be obtained, stored, and accessed for use in simultaneously determining liquid and gas mass flow rates within a two-phase flow.

In FIG. 2, it should be understood that the various components of the digital transmitter 104 are in communication with one another, although communication links are not explicitly illustrated, for the sake of clarity. Further, it should be understood that conventional components of the digital transmitter 104 are not illustrated in FIG. 2, but are assumed to exist within, or be accessible to, the digital transmitter 104. For example, the digital transmitter 104 will typically include (bulk) density and mass flow rate measurement systems, as well as drive circuitry for driving the driver 210.

Figure 3:
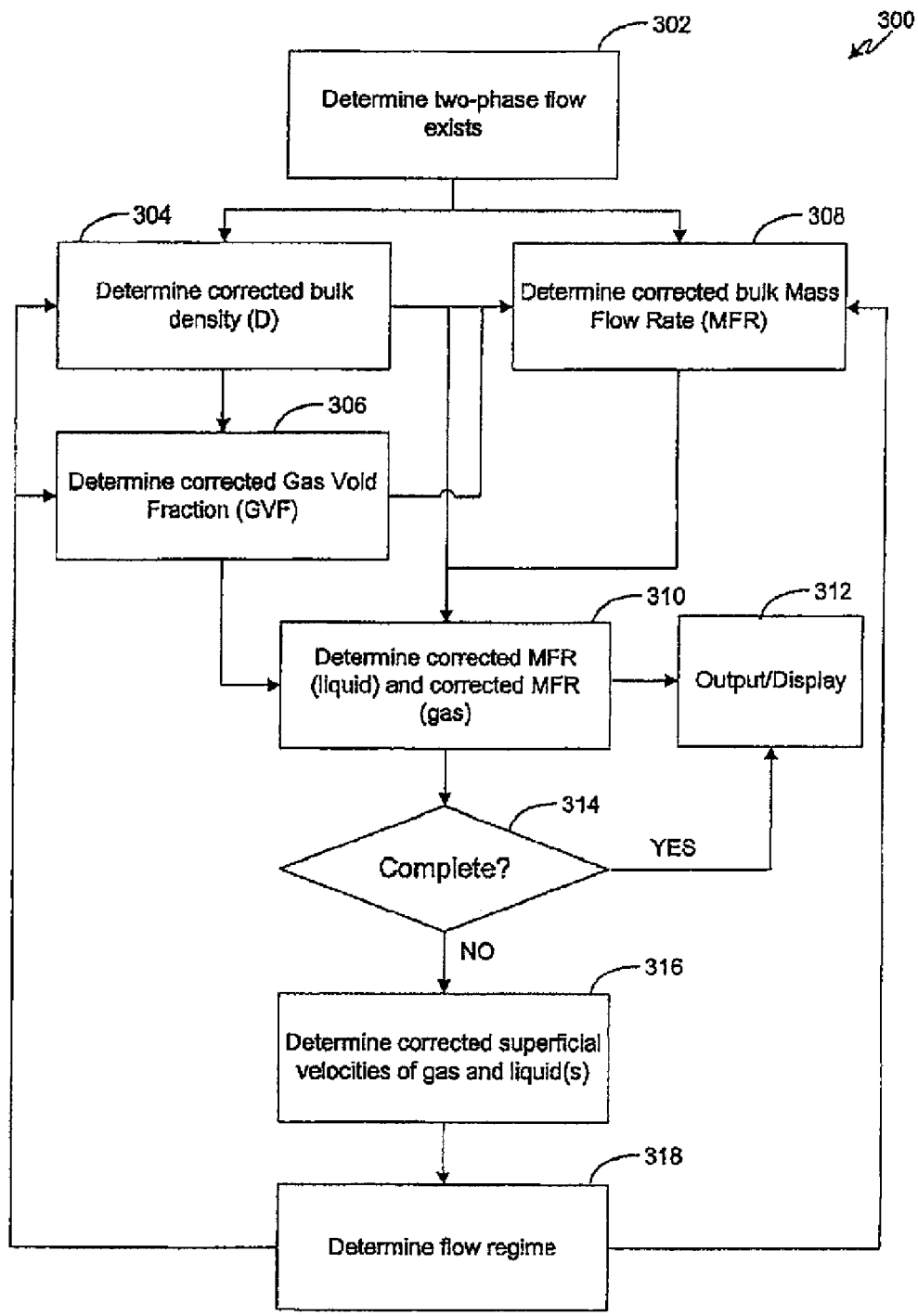
FIG. 3 is a flowchart illustrating an operation of the coriolis flowmeter of FIG. 2.

FIG. 3 is a flowchart 300 illustrating an operation of the coriolis flowmeter 200 of FIG. 2. Specifically, FIG. 3 illustrates techniques by which the flowmeter 200 of FIG. 2 is operable to simultaneously determine liquid and gas flow rates $MF_{liquid}$ and $MF_{gas}$ for a two-phase flow.

In FIG. 3, it is determined that a gas/liquid two-phase flow exists in the flowtube 215 (302). This can be done, for example, by an operator during configuration of the mass flowmeter/densitometer for gas/liquid flow. As another example, this determination may be made automatically by using a feature of the coriolis meter to detect that a condition of two-phase gas-liquid flow exists. In the latter case, such techniques are described in greater detail in, for example, U.S. Pat. No. 6,311,136 and U.S. Pat. No. 6,505,519, incorporated by reference above.

Once the existence of two-phase flow is established, a corrected bulk density $\rho_{true}$ is established (304) by the density correction system 240, using the density correction database 245 of the transmitter 104. That is, an indicated density apparent is corrected to obtain $\rho_{true}$. Techniques for performing this correction are discussed in more detail below.

Once $\rho_{true}$ is determined, a corrected gas void fraction $\rho_{true}$ may be determined (306) by the void fraction determination/correction system 260. Also, a corrected bulk mass flow rate $MF_{true}$ is determined (308) by the mass flow rate correction system 250. As with density, techniques for obtaining the corrected void fraction $\alpha_{true}$ and mass flow rate $MF_{true}$ are discussed in more detail below.

In FIG. 3, it should be understood from the flowchart 300 that the determinations of $\rho_{true}$, $\alpha_{true}$, and $MF_{true}$ may occur in a number of sequences. For example, in one implementation, the corrected void fraction $\alpha_{true}$ is determined based on previously-calculated corrected density $\rho_{true}$, whereupon the corrected mass flow rate $MF_{true}$ is determined based on $\alpha_{true}$. In another implementation, $\alpha_{true}$ and $\rho_{true}$ may be calculated independently of one another, and/or $\rho_{true}$ and $MF_{true}$ may be calculated independently of one another.

Once corrected density $\rho_{true}$, corrected void fraction $\alpha_{true}$, and corrected mass flow rate $MR_{true}$ are known, then the mass flow rates of the gas and liquid components are determined (310) by the flow component mass flow rate determination system 265. Techniques for determining the liquid/gas component flow rates are discussed in more detail below with respect to FIG. 4.

Once determined, the liquid/gas component flow rates may be output or displayed (312) for use by an operator of the flowmeter. In this way, the operator is provided, perhaps simultaneously, with information about both the liquid mass flow rate $MF_{liquid}$ and the gas mass flow rate $MF_{gas}$ of a two-phase flow.

In some instances, this determination may be sufficient (314), in which case the outputting of the liquid/gas component flow rates completes the process flow. However, in other implementations, the determination of the individual component mass flow rates may be improved upon by factoring in information about, for example, the superficial velocities of the gas/liquid components, the flow regime(s) of the flow, and phase slip, if any, between the components.

In particular, superficial velocities of the gas and liquid, $SV_{gas}$ and $SV_{liquid}$ are determined as follows. Gas superficial velocity $SV_{gas}$ is defined as:

$$SV_{gas}=MF_{gas}/(\rho_{gas}*A_T) \qquad \text{Eq. 1}$$

where the quantity $A_T$ represents a cross-section area of the flowtube 215, which may be taken at a point where a void fraction of the flow is measured. Similarly, a liquid superficial velocity $SV_{liquid}$ is defined as:

$$SV_{liquid}=MF_{liquid}/(\rho_{liquid}*A_T) \qquad \text{Eq. 2}$$

As shown in Eqs. 1 and 2, determination of superficial velocities in this context relies on the earlier determination of $MF_{gas}$ and $MF_{liquid}$. It should be understood from the above description and from FIG. 3 that $MF_{gas}$ and $MF_{liquid}$ represent corrected or true mass flow rates, $MF_{gas}^{true}$ and $MF_{liquid}^{true}$ since these factors are calculated based on $\rho_{true}$, $\alpha_{true}$, and $MF_{true}$. As a result, the superficial velocities $SV_{gas}$ and $SV_{liquid}$ represent corrected values $SV_{gas}^{true}$ and $SV_{liquid}^{true}$. Further, the density values $\rho_{gas}$ and $\rho_{liquid}$ refer, as above, to known densities of the liquid and gas in question, which may be stored in the density correction database 245. As discussed in more detail below with respect to techniques for calculating corrected density $\rho_{true}$, the density values $\rho_{gas}$ and $\rho_{liquid}$ may be known as a function of existing temperature or pressure, as detected by temperature sensor 220 and pressure sensor 225.

Using the superficial velocities and other known or calculated factors, some of which may be stored in the flow regime maps database 280, a relevant flow regime and/or phase slip may be determined (318) by the flow regime determination/correction system 275. Once superficial velocities, flow regime, and phase slip are known, further corrections may be made to the corrected bulk density $\rho_{true}$, corrected bulk mass flow rate $MF_{true}$, and/or corrected void fraction $\alpha_{true}$. In this way, as illustrated in FIG. 3, component flow rates $MF_{gas}$ and $MF_{liquid}$ may be determined.

Flow regime(s) in two phase liquid/gas flow may be described by contours on a graph plotting the liquid superficial velocity versus the gas superficial velocity. As just described, an improvement to determinations of $\rho_{true}$, $\alpha_{true}$, and/or $MF_{true}$ may be obtained by first establishing an approximate value of the liquid and gas flow rates, and then applying a more detailed model for the flow regime identified. For example, at relatively low GVF and relatively high flow there exists a flow regime in which the aerated fluid behaves as a homogenous fluid with little or no errors in both density and mass flow. This can be detected as homogenous flow requiring no correction, simply using observation of the drive gain, which shows little or no increase in such a setting, despite a significant drop in observed density.

Figure 4:
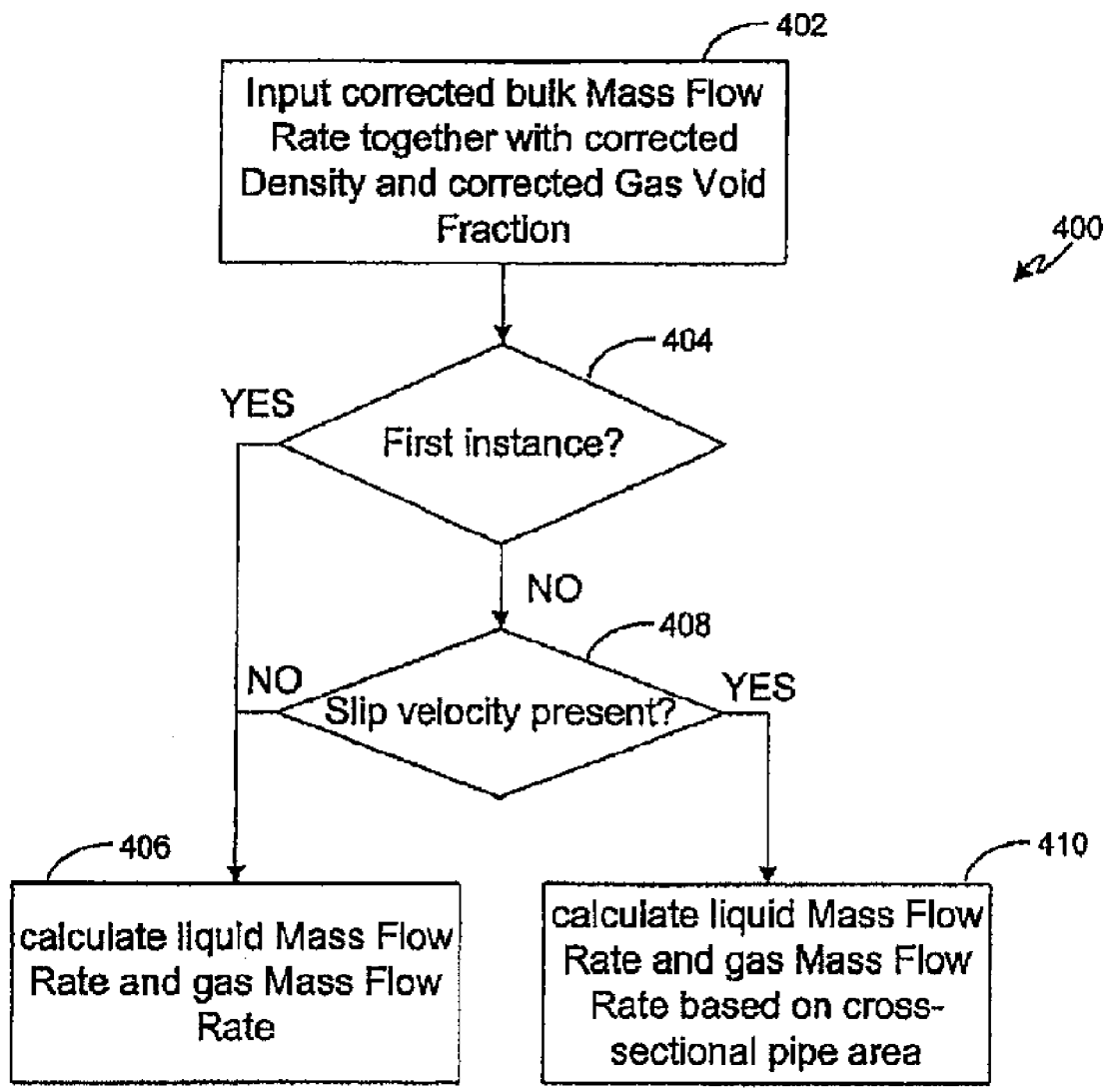
FIG. 4 is a flowchart illustrating techniques for determining liquid and gas flow rates for a two-phase flow.

FIG. 4 is a flowchart 400 illustrating techniques for determining liquid and gas flow rates $MF_{liquid}$ and $MF_{gas}$ for a two-phase flow. That is, the flowchart 400 generally represents one example of techniques for determining liquid and gas flow rates (310), as described above with respect to FIG. 3.

In FIG. 4, the determination of liquid and gas flow rates (310) begins with inputting the corrected density, void fraction, and mass flow rate factors $\rho_{true}$, $\alpha_{true}$, and $MF_{true}$ (402). In a first instance, (404), the liquid and gas flow rates are determined (406) using Eqs. 3 and 4:

$$MF_{gas}=\alpha_{true}(\rho_{gas}/\rho_{true})(MF_{true}) \qquad \text{Eq. 3}$$

$$MF_{liquid}=(1-\alpha_{true})(\rho_{liquid}/\rho_{true})(MF_{true}) \qquad \text{Eq. 4}$$

Eqs. 3 and 4 assume that there is no slip velocity (i.e., phase slip) between the liquid and gas phases (i.e., average velocity of the gas phase, $AV_{gas}$, and average velocity of the liquid phase, $AV_{liquid}$, are equal). This assumption is consistent with the fact that, in the first instance, superficial velocities and flow regimes (and therefore, phase slip) have not been determined.

In the second instance and thereafter (404), a determination is made, perhaps by the flow regime determination/correction system 275, as to whether phase slip exists (408). If not, then Eqs. 3 and 4 are used again (406) or the process ends.

If phase slip does exist (408), defined above as $S=AV_{gas}/AV_{liquid}$, the terms $MF_{gas}$ and $MF_{liquid}$ are calculated using the cross-sectional area of the flowtube 215, $A_T$, as also used in the calculation of superficial velocities in Eqs. 1 and 2 (410). Using the definition of slip S just given, $$MF_{gas} = \rho_{gas}(\alpha_{true} A_T)(AV_{gas}) = \rho_{gas}(\alpha_{true} A_T)(S)(AV_{liquid}) \quad \text{Eq. 5}$$

$$MF_{liquid} = \rho_{liquid}((1-\alpha_{true})A_T)(AV_{liquid}) \quad \text{Eq. 6}$$

Since $MF_{true} = MF_{gas} + MF_{liquid}$, Eqs. 5 and 6 may be solved for $AV_{liquid}$ to obtain Eq. 7:

$$AV_{liquid} = MF_{true}/(A_T(\rho_{gas}\alpha_{true}S + \rho_{liquid}(1-\alpha_{true}))) \quad \text{Eq. 7}$$

As a result, the liquid and gas flow rates are determined (406) using Eqs. 8 and 9:

$$MF_{liquid} = [\rho_{liquid}(1-\alpha_{true})/(\rho_{gas}\alpha_{true}S + \rho_{liquid}(1-\alpha_{true}))][MF_{true}] \quad \text{Eq. 8}$$

$$MF_{gas} = MF_{true} - MF_{liquid} \quad \text{Eq. 9}$$

As described above, gas entrained in liquid forms a two-phase flow. Measurements of such a two-phase flow with a Coriolis flowmeter result in indicated parameters $\rho_{apparent}$, $\alpha_{apparent}$, and $MF_{apparent}$ for density, void fraction, and mass flow rate, respectively, of the two-phase flow. Due to the nature of the two-phase flow in relation to an operation of the Coriolis flowmeter, these indicated values are incorrect by a predictable factor. As a result, the indicated parameters may be corrected to obtain actual parameters $\rho_{true}$, $\alpha_{true}$, and $MF_{true}$. In turn, the actual, corrected values may be used to simultaneously determine individual flow rates of the two (gas and liquid) components.

Figure 5A:
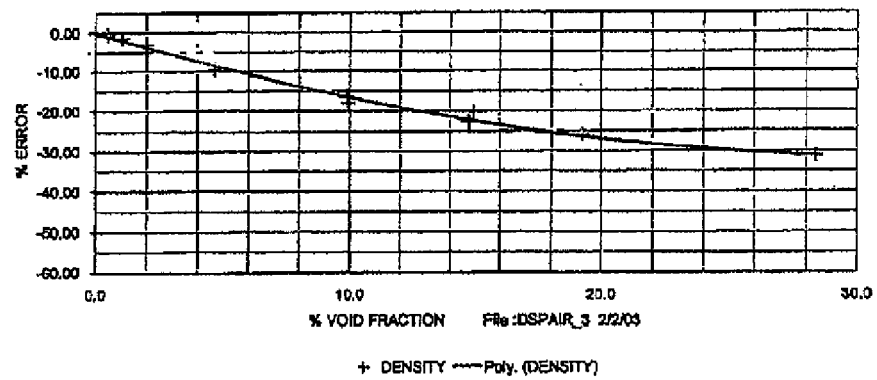
FIGS. 5A and 5B are graphs illustrating a percent error in a measurement of void fraction and liquid fraction, respectively.
Figure 5B:
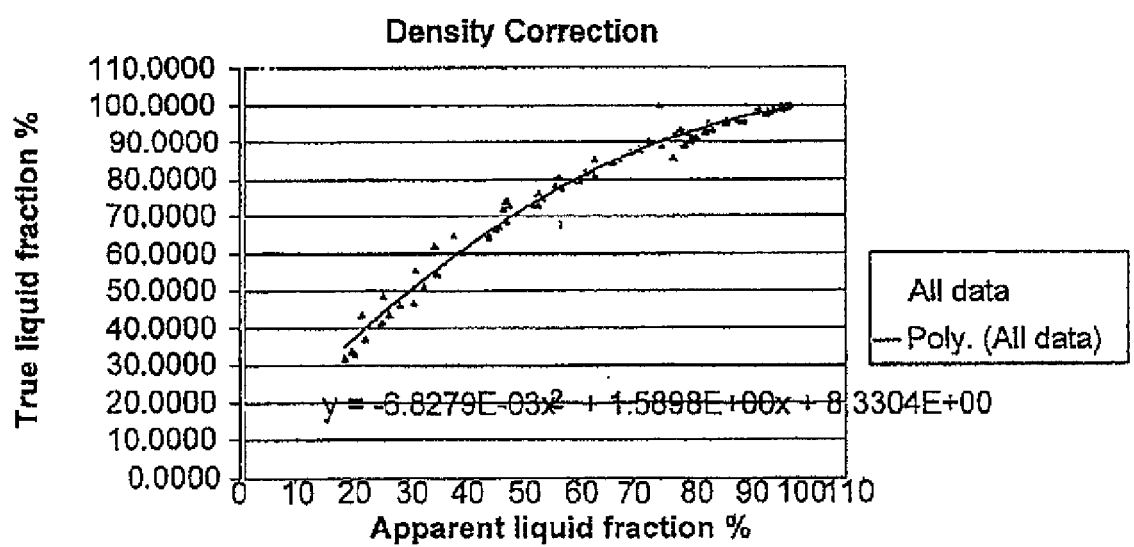

FIGS. 5A and 5B are graphs illustrating a percent error in a measurement of void fraction and liquid fraction, respectively. In FIG. 5A, the percent error is a density percent error that is dependent on various design and operational parameters, and generally refers to the deviation of the apparent (indicated) density from the true combined density that would be expected given the percentage (%) of gas in liquid.

In FIG. 5B, true liquid fraction versus indicated liquid fraction is illustrated. FIG. 5B shows the results, for the relevant flowmeter design, of several line sizes and flow rates. In more general terms, the functional relationship may be more complex and depend on both line size and flowrate. In FIG. 5B, a simple polynomial fit is shown that can be used to correct the apparent liquid fraction.

Figure 6:
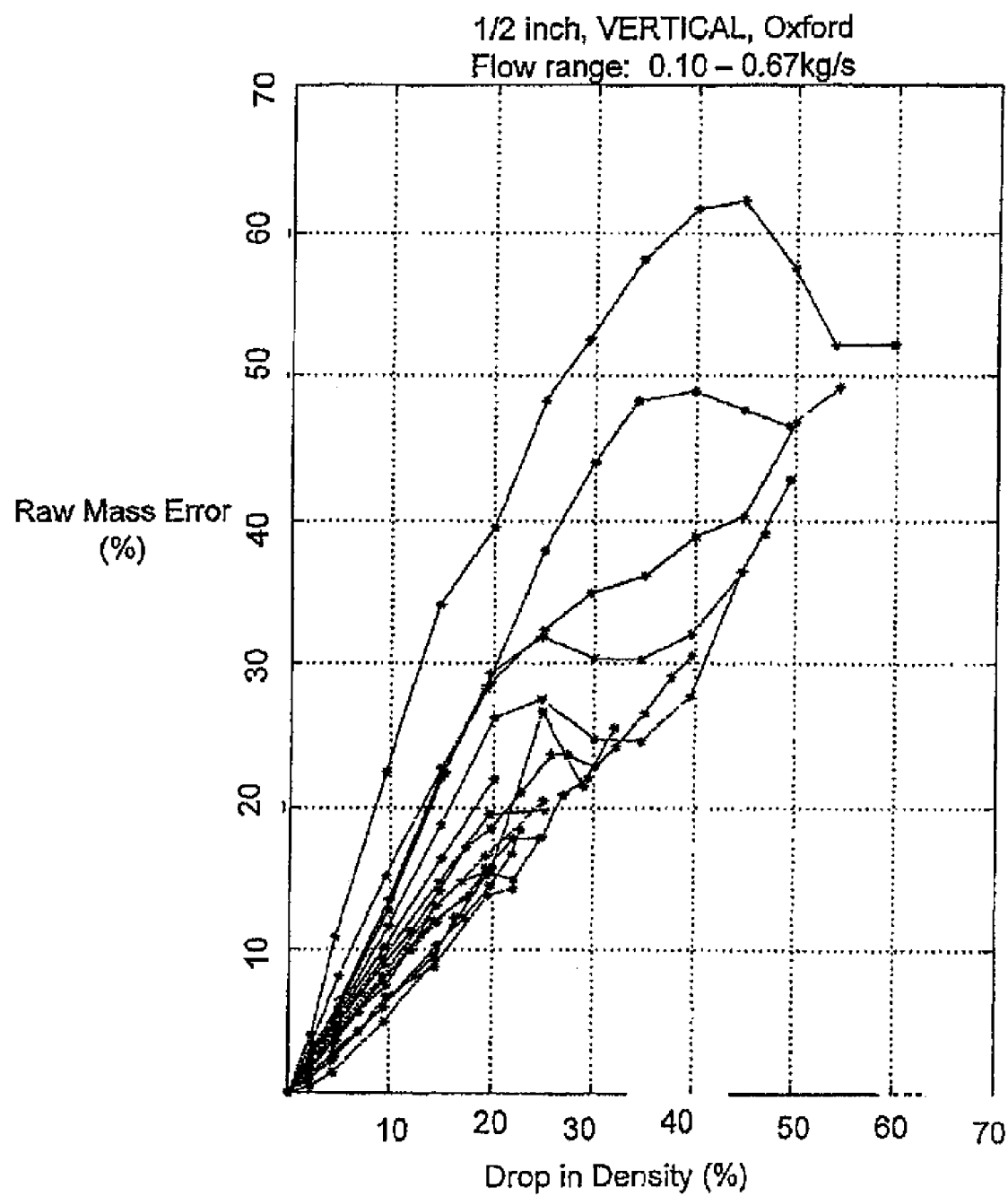
FIG. 6 is a graph illustrating a mass flow error as a function of a drop in density for a flowtube having a particular orientation and over a selected flow range.

Other graphing techniques may be used; for example, true void fraction may be plotted against indicated void fraction. For example, FIG. 6 is a graph illustrating a mass flow error as a function of a drop in density for a flowtube having a particular orientation and over a selected flow range.

Figure 7:
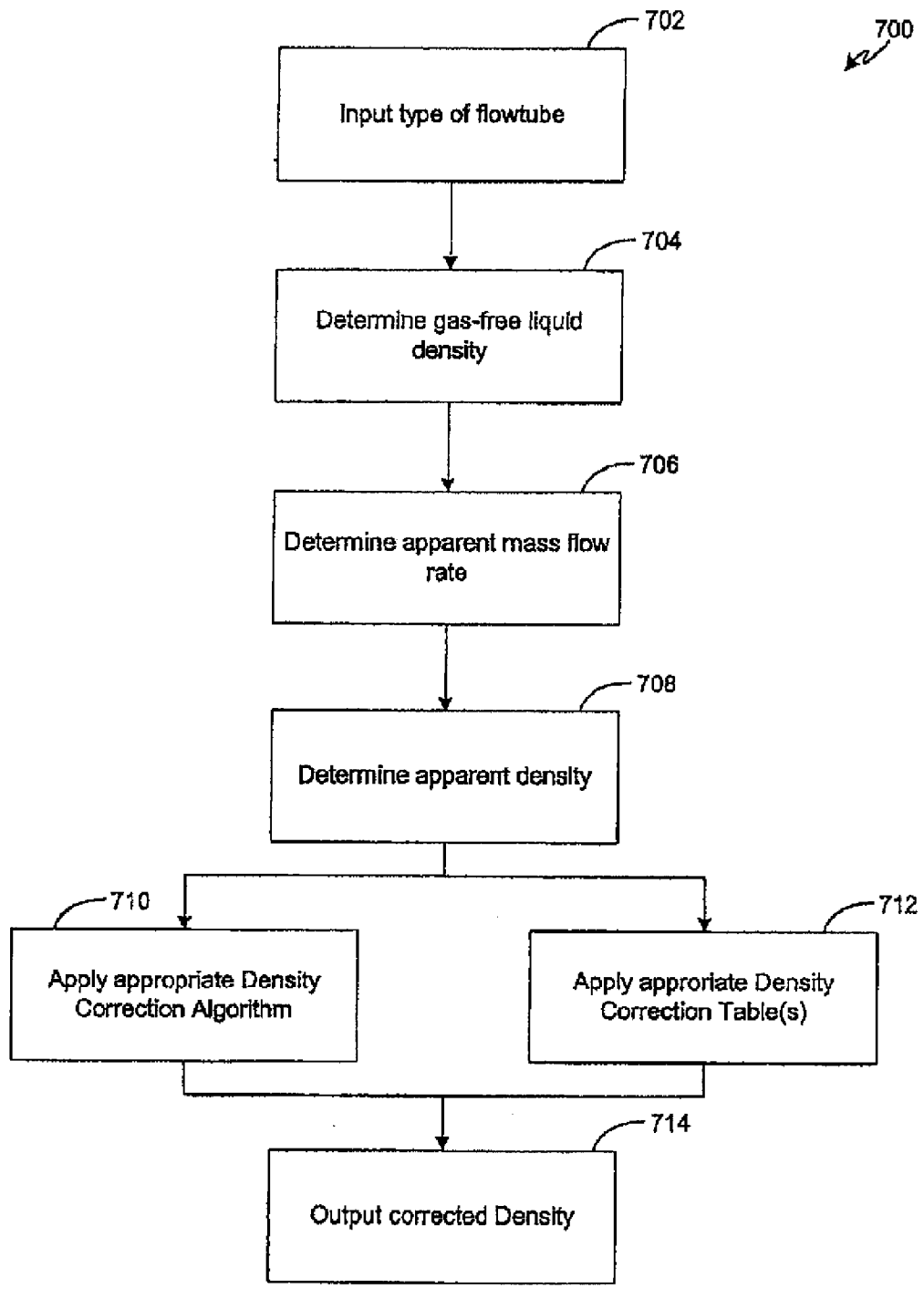
FIG. 7 is a flowchart illustrating techniques for correcting density measurements.

FIG. 7 is a flowchart 700 illustrating techniques for correcting density measurements (304 in FIG. 3). In FIG. 7, the process begins with an inputting of the type of flowtube 215 being used (702), which may include, for example, whether the flowtube 215 is bent or straight, as well as other relevant facts such as a size or orientation of the flowtube 215.

Next, a gas-free density of the liquid, $\rho_{liquid}$ is determined (704). This quantity may be useful in the following calculation(s), as well as in ensuring that that other factors that may influence the density measurement $\rho_{apparent}$, such as temperature, are not misinterpreted as void fraction effects. In one implementation, the user may enter the liquid density $\rho_{liquid}$ directly, along with a temperature dependence of the density. In another implementation, known fluids (and their temperature dependencies) may be stored in the density correction database 245, in which case the user may enter a fluid by name. In yet another implementation, the flowmeter 200 may determine the liquid density during a time of single-phase, liquid flow, and store this value for future use.

An indicated mass flow rate $MF_{apparent}$ is read from the Coriolis meter (706), and then an indicated density $\rho_{apparent}$ is read from the Coriolis meter (708). Next, the density correction system 240 applies either a theoretical, algorithmic (710) or empirical, tabular correction (712) to determine the true density $\rho_{true}$ of the gas/liquid mixture. The quantity $\rho_{true}$ may then be output as the corrected density (714).

An algorithmic density correction (710) may be determined based on the knowledge that, if there were no effect of the two-phase flow from the normal operation of a Coriolis meter when used to measure density, the indicated density would drop by an amount derived from the equation describing void fraction, which is set forth above in terms of volume flow and repeated here in terms of density as Eq. 10:

$$\alpha_{(\%)} = [(\rho_{apparent} - \rho_{liquid})/(\rho_{gas} - \rho_{liquid})] \times 100 \quad \text{Eq. 10}$$

This can be used to define a quantity "density drop," or $\Delta\rho$, as shown in Eq. 11:

$$\Delta\rho = (\rho_{apparent} - \rho_{liquid}) = \alpha_{(\%)} \times (\rho_{gas} - \rho_{liquid})/100 \quad \text{Eq. 11}$$

Note that Eq. 11 shows the quantity $\Delta\rho$ as being positive; however, this quantity could be shown as a negative drop simply by multiplying the right-hand side of the equation by −1, resulting in Eq. 12:

$$\Delta\rho = (\rho_{liquid} - \rho_{apparent}) = \alpha_{(\%)} \times (\rho_{liquid} - \rho_{gas})/100 \quad \text{Eq. 12}$$

The quantity $\rho_{gas}$ may be small compared to $\rho_{liquid}$, in which case Eq. 12 may be simplified to Eq. 13:

$$\Delta\rho = (\rho_{liquid} - \rho_{apparent}) = \alpha_{(\%)} \times \rho_{liquid}/100 \quad \text{Eq. 13}$$

As discussed extensively above, density measurements by a Coriolis meter, or any vibrating densitometer, generally are under-reported by the meter, and require correction. Accordingly, under two-phase flow Eqs. 12 or 13 may thus be used to define the following two quantities: a corrected or true density drop, $\Delta\rho_{true}$, and an indicated or apparent density drop, $\Delta\rho_{app}$. Using Eq. 13 as one example, this results in Eqs. 14 and 15:

$$\Delta\rho_{true} = (\rho_{liquid} - \rho_{true}) = \alpha_{(\%)} \times \rho_{liquid}/100 \quad \text{Eq. 14}$$

$$\Delta\rho_{app} = (\rho_{liquid} - \rho_{apparent}) = \alpha_{(\%)} \times \rho_{liquid}/100 \quad \text{Eq. 15}$$

There can be derived or empirically determined a relationship between $\Delta\rho_{true}$ and $\Delta\rho_{apparent}$ and apparent mass flow rate, $MF_{apparent}$, as well as other parameters, such as, for example, drive gain, sensor balance, temperature, phase regime, etc.). This relationship can be expressed as shown as $\Delta\rho_{true} = f(MF_{apparent},$ drive gain, sensor balance, temperature, phase regime, and/or other factors).

As a result, the relationship may generally be derived, or at least proven, for each flowtube in each setting. For one model flowtube, known and referred to herein as the Foxboro/Invensys CFS10 model flowtube, it has been empirically determined that for some conditions the above functional relationship can be simplified to be only a function $\Delta\rho_{apparent}$ and of the form shown in Eq. 16:

$$\Delta\rho_{true} = \sum_{i=0}^{M} a_i (\Delta\rho_{apparent})^i \qquad \text{Eq. 16}$$

To force the condition for both sides of Eq. 16 to be zero when there is no apparent density drop relationship results in Eq. 17:

$$\Delta\rho_{true} = \sum_{i=1}^{M} a_i (\Delta\rho_{apparent})^i \qquad \text{Eq. 17}$$

M generally depends on the complexity of the empirical relationship, but in many cases can be as small as 2 (quadratic) or 3 (cubic).

Figure 9:
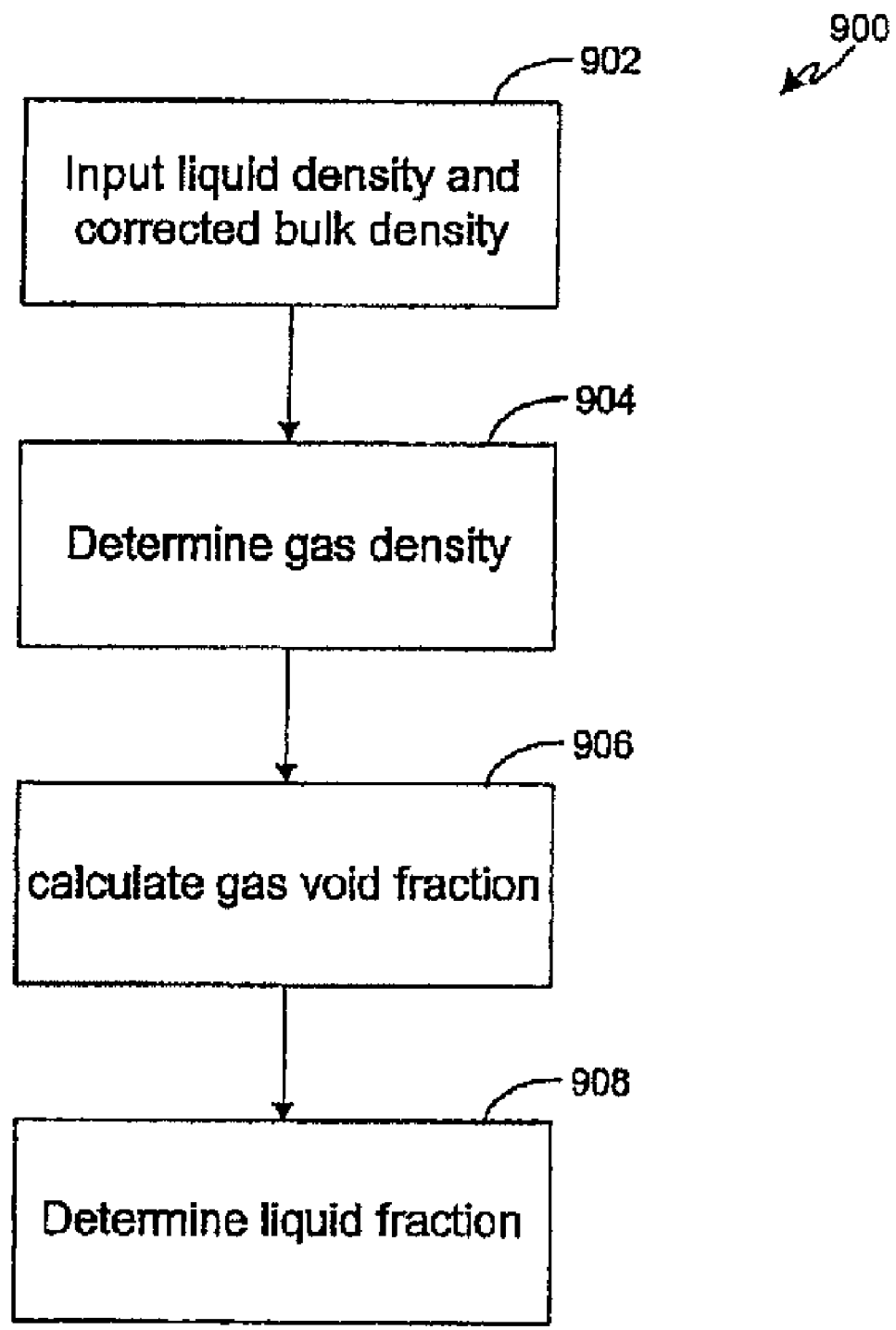
FIG. 9 is a flowchart illustrating techniques for determining void fraction measurements.

Once the true density drop is determined, then working back through the above equations it is straightforward to derive the true mixture density $\rho_{true}$, as well as the true liquid and gas (void) fractions (the latter being discussed in more detail with respect to FIG. 9).

Figure 8:
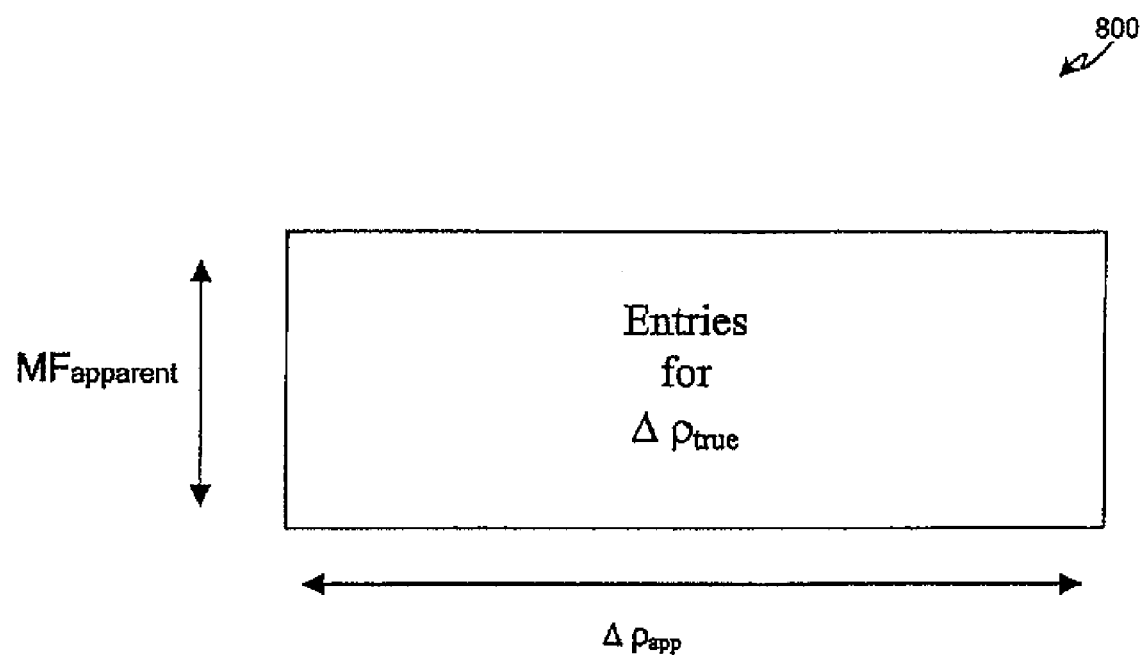
FIG. 8 is a table showing a relationship between an apparent density drop and an apparent mass flow rate of the two-phase flow.

A tabular correction for density (712) may be used when, for example, a functional relationship is too complex or inconvenient to implement. In such cases, knowledge of the quantities $\Delta\rho_{apparent}$ and $\Delta MF_{apparent}$ may be used to determine $\Delta\rho_{true}$ by employing a table having the form of a table 800 of FIG. 8.

The table 800 may be, for example, a tabular look-up table that can be, for example, stored in the database 245, or in another memory, for use across multiple applications of the table. Additionally, the table may be populated during an initialization procedure, for storage in the database 245 for an individual application of the table.

It should be understood that either or both of the algorithmic and tabular forms may be extended to include multiple dimensions, such as, for example, gain, temperature, balance, or flow regime. The algorithmic or tabular correction also may be extended to include other surface fitting techniques, such as, for example, neural net, radical basis functions, wavelet analyses, or principle component analysis.

As a result, it should be understood that such extensions may be implemented in the context of FIG. 3 during the approach described therein. For example, during a first instance, density may be determined as described above. Then, during a second instance, when a flow regime has been identified, the density may be further corrected using the flow regime information.

FIG. 9 is a flowchart 900 illustrating techniques for determining void fraction measurements (306 in FIG. 3). In FIG. 9, the process begins with an inputting by the void fraction determination system 240 of the previously-determined liquid and bulk (corrected) densities, $\rho_{liquid}$ and $\rho_{true}$ (902).

A density of the gas, $\rho_{gas}$ is then determined (904). As with the liquid density $\rho_{liquid}$, there are several techniques for determining $\rho_{gas}$. For example, $\rho_{gas}$ may simply be assumed to be a density of air, generally at a known pressure, or may be an actual known density of the particular gas in question. As another example, this known density $\rho_{gas}$ may be one of the above factors (i.e., known density of air or the specific gas) at an actual or calculated pressure, as detected by the pressure sensor 225, and/or at an actual or calculated temperature, as detected by the temperature sensor 220. The temperature and pressure may be monitored using external equipment, as shown in FIG. 2, including the temperature sensor 220 and/or the pressure sensor 225.

Further, the gas may be known to have specific characteristics with respect to factors including pressure, temperature, or compressibility. These characteristics may be entered along with an identification of the gas, and used in determining the current gas density $\rho_{gas}$. As with the liquid(s), multiple gasses may be stored in memory, perhaps along with the characteristics just described, so that a user may access density characteristics of a particular gas simply by selecting the gas be name from a list.

Once the factors $\rho_{liquid}$, $\rho_{gas}$, and $\rho_{true}$ are known, then it should be clear from Eq. 10 that void fraction $\alpha_{true}$ may be easily determined (906). Then, if needed, liquid fraction may be determined (908) simply by calculating $1-\alpha_{true}$.

Although the above discussion presents techniques for determining void fraction $\alpha_{true}$ based on density, it should be understood that void fraction may be determined by other techniques. For example, an indicated void fraction $\alpha_{apparent}$ may be directly determined by the Coriolis flowmeter, perhaps in conjunction with other void fraction determination systems (represented by the void fraction sensor 235 of FIG. 2), and then corrected based on empirical or derived equations to obtain $\alpha_{true}$. In other implementations, such external void fraction determining systems may be used to provide a direct measurement of $\alpha_{true}$.

Figure 10:
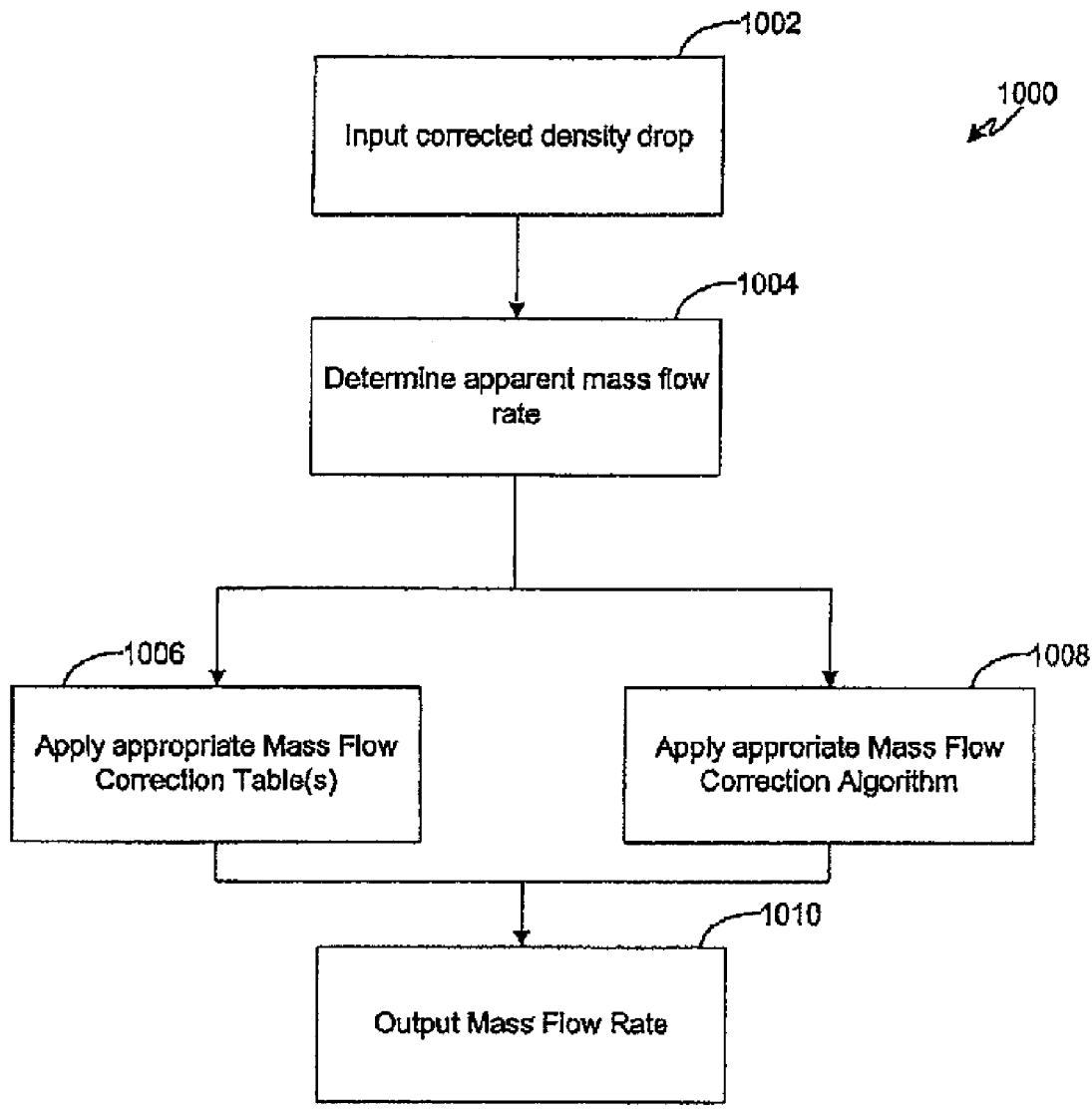
FIG. 10 is a flowchart illustrating techniques for determining corrected mass flow rate measurements.

FIG. 10 is a flowchart 1000 illustrating techniques for determining corrected mass flow rate measurements (308 in FIG. 3). In FIG. 10, the mass flow rate correction system 250 first inputs the previously-calculated corrected density drop $\Delta\rho_{true}$ (1002), and then inputs a measured, apparent mass flow rate $MF_{apparent}$ (1004).

The mass flow rate correction system 250 applies either a tabular (1006) or algorithmic correction (1008) to determine the true mass flow rate $MF_{true}$ of the gas/liquid mixture. The quantity $MF_{true}$ may then be output as the corrected mass flow rate (1010).

Figure 11:
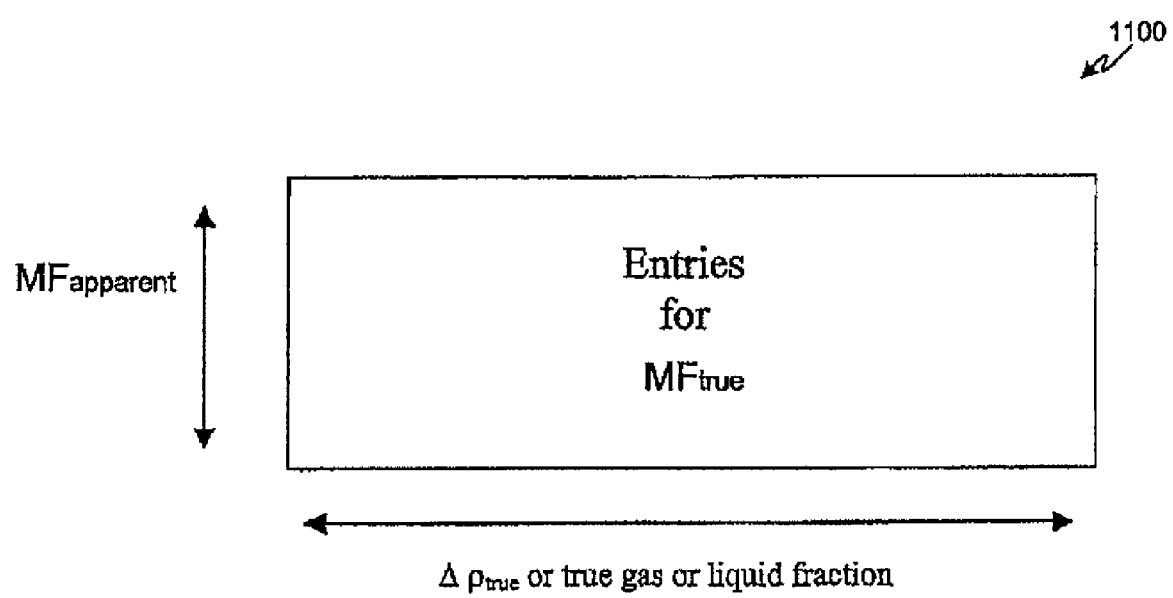
FIG. 11 is a table showing a relationship between an apparent mass flow rate and a corrected density drop of the two-phase flow.

In applying the tabular correction for mass flow rate (1006), knowledge of the quantities $\Delta\rho_{true}$ and $\Delta MF_{apparent}$ may be used to determine $MF_{true}$ by employing a table having the form of a table 1100 of FIG. 11.

The table 1100, as with the table 800 may be, for example, a tabular look-up table that can be, for example, stored in the database 245, or in another memory, for use across multiple applications of the table. Additionally, the table may be populated during an initialization procedure, for storage in the database 255 for an individual application of the table.

Normalized values $MF_{norm\_app}$ and $MF_{norm\_true}$ may be used in place of the actual ones shown above, in order to cover more than one size coriolis flowtube. Also, the entries can be in terms of the correction, where the correction is defined by Eq. 18:

$$\Delta MF = MF_{true} - MF_{apparent} \qquad \text{Eq. 18}$$

The values in Eq. 18 should be understood to represent either actual or normalized values.

In an algorithmic approach, as with density, the correction for mass flow may be implemented by way of a theoretical or an empirical functional relationship that is generally understood to be of the form $\Delta MF = f(MF_{apparent}$, void fraction, drive gain, sensor balance, temperature, phase regime, and/or other factors).

For some cases the function can simplify to a polynomial, such as, for example, the polynomial shown in Eq. 19:

$$\Delta MF = \sum_{i=0}^{M} \sum_{j=0}^{N} a_i b_j (\Delta \rho_{true}^i)(MF_{norm\_app}^j) \qquad \text{Eq. 19}$$

For some set of conditions, the functional relationship can be a combination of a polynomial and exponential, as shown in Eq. 20:

$$\Delta MF = a_1 d e^{(a_2 d^2 + a_3 d + a_4 m^2 + a_5 m)} + a_6 d^2 + a_7 d + a_8 m^2 + a_9 m \qquad \text{Eq. 20}$$

In Eq. 20, $d = \Delta \rho_{true}$, and $m = f(MF_{apparent})$.

In one implementation, m in Eq. 20 may be replaced by apparent superficial liquid velocity $SV_{liquid}$ which is given as described above by Eq. 2 as $SV_{liquid} = MF_{liquid}(\rho_{liquid} * A_T)$. In this case, $\rho_{liquid}$ and flowtube cross-section $A_T$ are known or entered parameters, and may be real-time corrected for temperature using, for example, the on-board temperature measurement device 220 of the digital controller/transmitter 104.

It should be understood that, as with the density corrections discussed above, either or both of the algorithmic and tabular forms may be extended to include multiple dimensions, such as, for example, gain, temperature, balance, or flow regime. The algorithmic or tabular correction also may be extended to include other surface fitting techniques, such as, for example, neural net, radical basis functions, wavelet analyses, or principle component analysis.

As a result, it should be understood that such extensions may be implemented in the context of FIG. 3 during the approach described therein. For example, during a first instance, mass flow rate may be determined as described above. Then, during a second instance, when a flow regime has been identified, the mass flow rate may be further corrected using the flow regime information.

All of the above functional relationships for mass flow rate may be restated using gas fraction (α) or liquid fraction (100−α) instead of density drop, as reflected in the table 1100 of FIG. 11. Also, although the above described methods are dependent on knowledge of the corrected density drop $\Delta \rho_{true}$, it should be understood that other techniques may be used to correct an indicated mass flow rate. For example, various techniques for correcting mass flow rate measurements of a two-phase flow are discussed in U.S. Pat. No. 6,505,519, incorporated by reference above.

Having described density, void fraction, and mass flow rate corrections above in general terms, for the purpose of, for example, simultaneously calculating individual flow component (phases) flow rates in a two-phase flow, the below discussion and corresponding figures provide specific examples of implementations of these techniques.

Figure 12:
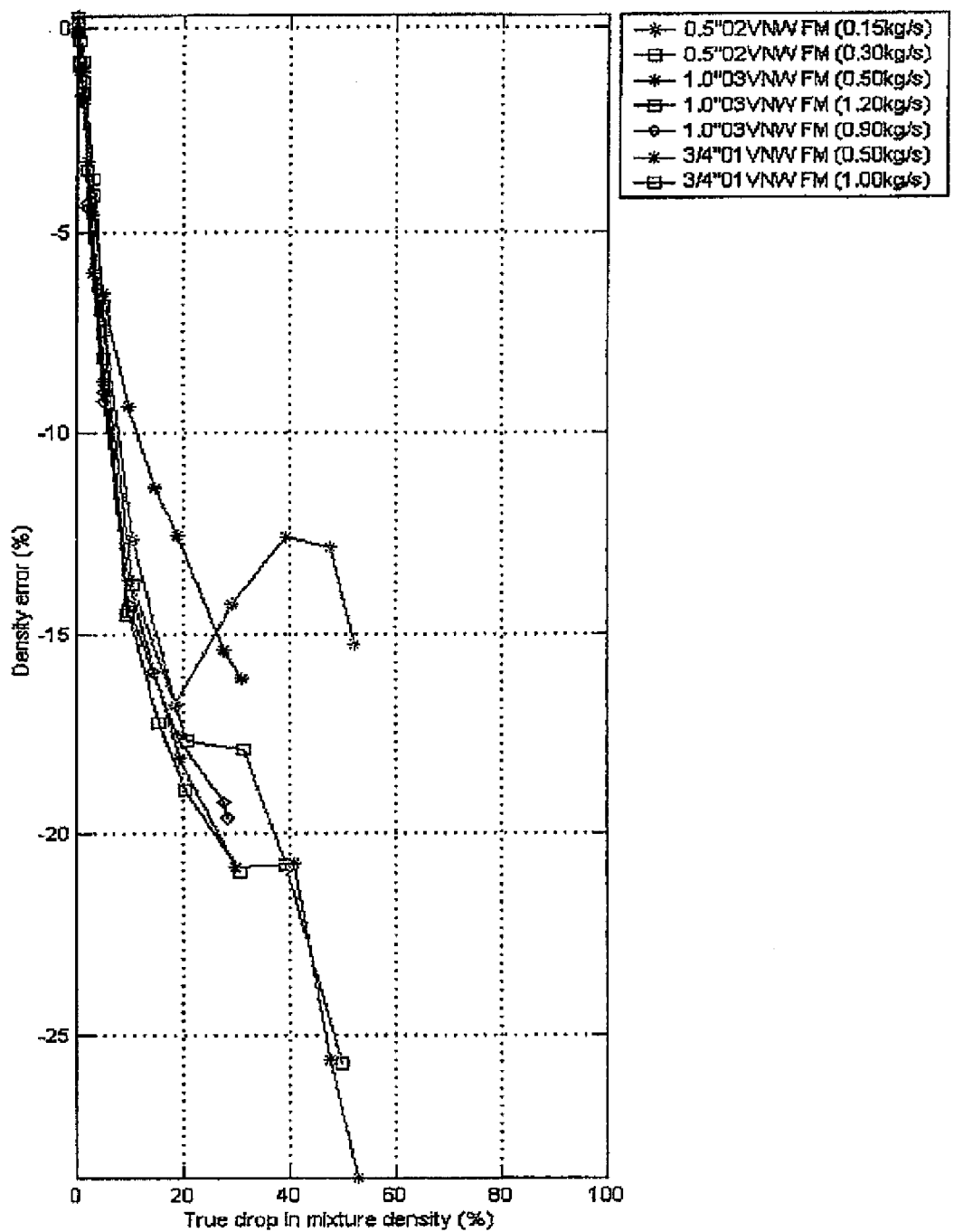
FIGS. 12-14 are graphs illustrating examples of density corrections for a number of flowtubes.

FIGS. 12-14 are graphs illustrating examples of density corrections for a number of flowtubes. In particular, the examples are based on data obtained from three vertical water flowtubes, the flowtubes being: ½", ¾", and 1" in diameter.

More specifically, the ½" data was taken with a 0.15 kg/s flow rate and a 0.30 kg/s flow rate; the ¾" data was taken with a 0.50 kg/s flow rate and a 1.00 kg/s flow rate; and the 1" data was taken with a 0.50 kg/s flow rate, a 0.90 kg/s flow rate, and a 1.20 kg/s flow rate. FIG. 12 illustrates an error, $e_d$, of the apparent density of the fluid-gas mixture (two-phase flow) versus the true drop in density of the fluid-gas mixture, $\Delta \rho_{true}$:

$$\Delta \rho_{true} = 100 \cdot \frac{\rho_{liquid} - \rho_{true}}{\rho_{liquid}} \qquad \text{Eq. 21}$$

-continued $$e_d = 100 \cdot \frac{\rho_{apparent} - \rho_{true}}{\rho_{true}} \qquad \text{Eq. 22}$$

where, as above, $\rho_{liquid}$ is the density of the gas-free liquid, $\rho_{true}$ is the true density of the liquid-gas mixture, and $\rho_{apparent}$ is the apparent or indicated density of the liquid-gas mixture.

In FIG. 12, the correction is performed in terms of the apparent drop in mixture density, $\Delta \rho_{apparent}$, as shown in Eq. 23:

$$\Delta \rho_{apparent} = 100 \cdot \frac{\rho_{liquid} - \rho_{apparent}}{\rho_{apparent}} \qquad \text{Eq. 23}$$

In FIG. 12, when fitting the data, both the apparent and true drop in density of the mixture were normalized to values between 0 and 1 by dividing them through by 100, where this normalization is designed to ensure numerical stability of the optimization algorithm. In other words, the normalized apparent and true drop in mixture density are the apparent and true drop in mixture density defined as a ratio, rather than as a percentage, of the liquid density $\rho_{liquid}$, as shown in Eq. 24:

$$\Delta \rho_{apparent}^{normalized} = \frac{\Delta \rho_{apparent}}{100} \qquad \text{Eq. 24}$$

The model formula, based on Eq. 17, provides Eq. 25:

$$\Delta \rho_{true}^{normalized} = a_1 (\Delta \rho_{apparent}^{normalized})^3 + a_2 (\Delta \rho_{apparent}^{normalized})^2 + a_3 (\Delta \rho_{apparent}^{normalized}) \qquad \text{Eq. 25}$$

Figure 13A:
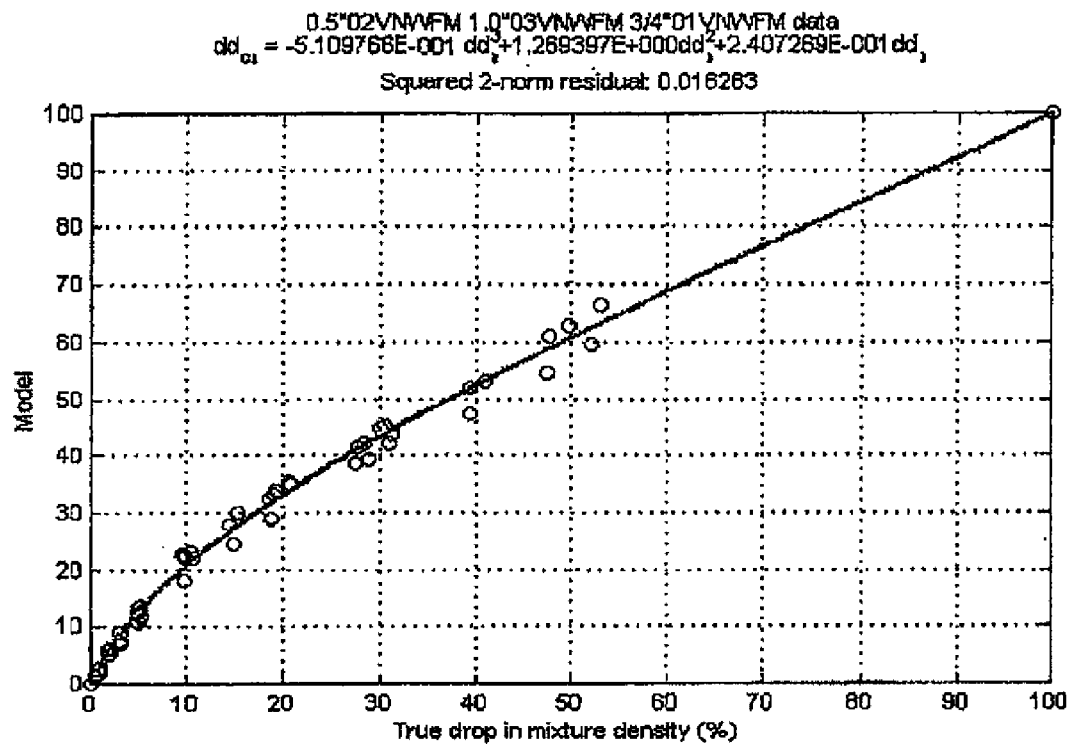
Figure 13B:
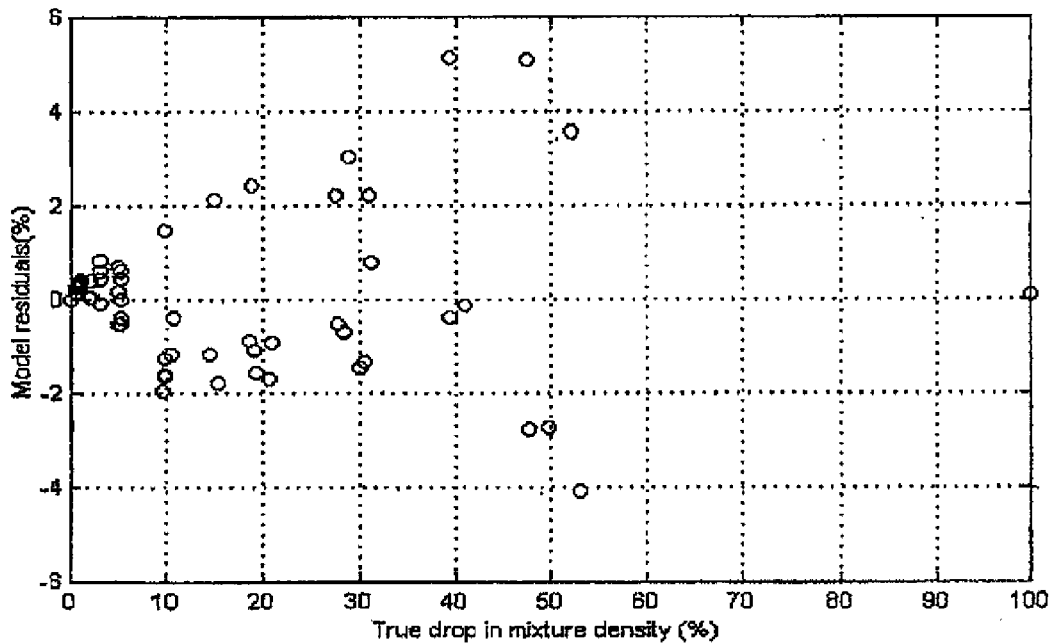
Figure 14A:
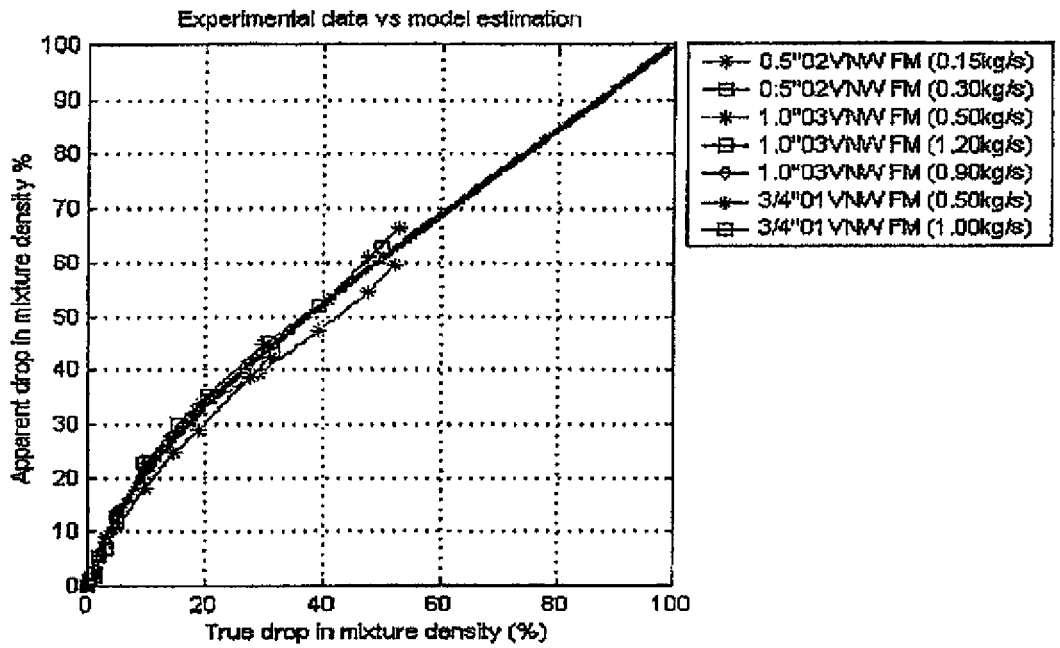
Figure 14B:
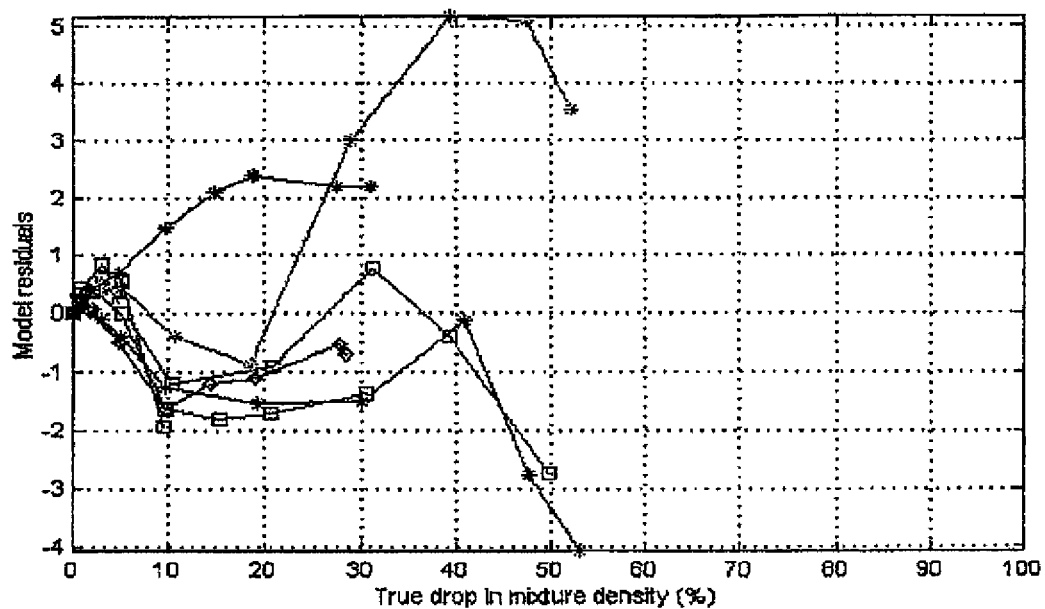

In this case, the coefficients are $a_1 = -0.51097664273685$, $a_2 = -1.26939674868129$, and $a_3 = 0.24072693119420$. FIGS. 13A and 13B illustrate the model with the experimental data and the residual errors, as shown. FIGS. 14A and 14B give the same information, but with each flow rate plotted separately.

To summarize, the drop in density correction is performed in the transmitter 104 by calculating the apparent density drop $\Delta \rho_{apparent}$, using the apparent density value $\rho_{apparent}$ and the liquid density $\rho_{liquid}$. The value of the apparent drop in density is normalized to obtain $$\Delta \rho_{apparent}^{normalized} = \frac{\Delta \rho_{apparent}}{100},$$

so that, as explained above, the drop in density is calculated as a ratio rather than a percentage. The density correction model(s) may then be applied to obtain the normalized corrected drop in mixture density $\Delta \pi_{true}^{normalized}$. Finally, this value is un-normalized to obtain the corrected drop in density $\Delta \rho_{true} = 100 \cdot \Delta \rho_{true}^{normalized}$. Of course, the final calculation is not necessary if the corrected drop in mixture density $\Delta \rho_{true}$ is defined as a ratio rather than percentage of the true value.

FIGS. 15-20 are graphs illustrating examples of mass flow rate corrections for a number of flowtubes. In particular, the examples are based on data obtained from three vertical water flowtubes, the flowtubes being: ½", ¾", and 1" in diameter. More specifically, the ½" data was taken with a 0.15 kg/s flow rate and a 0.30 kg/s flow rate; the ¾" data was taken with a 0.50 kg/s flow rate and a 1.00 kg/s flow rate; and the 1" data was taken with 18 flow rates between 0.30 kg/s and 3.0 kg/s flow rate, with a maximum drop in density of approximately 30%.

Figure 15A:
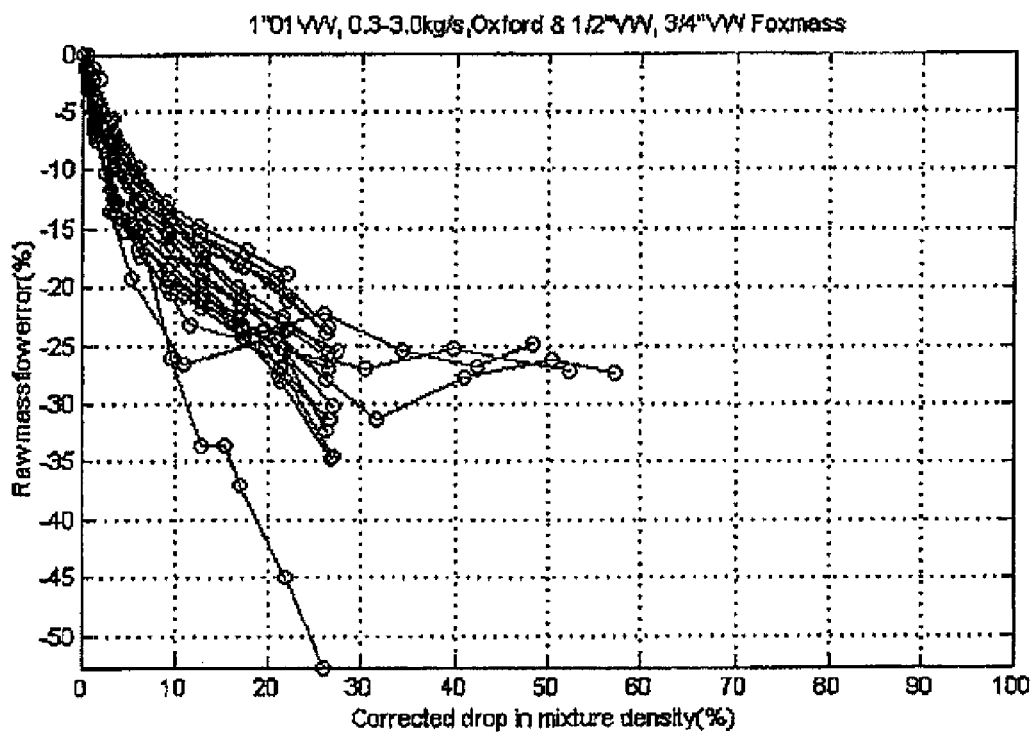
FIGS. 15-20 are graphs illustrating examples of mass flow rate corrections for a number of flowtubes.
Figure 15B:
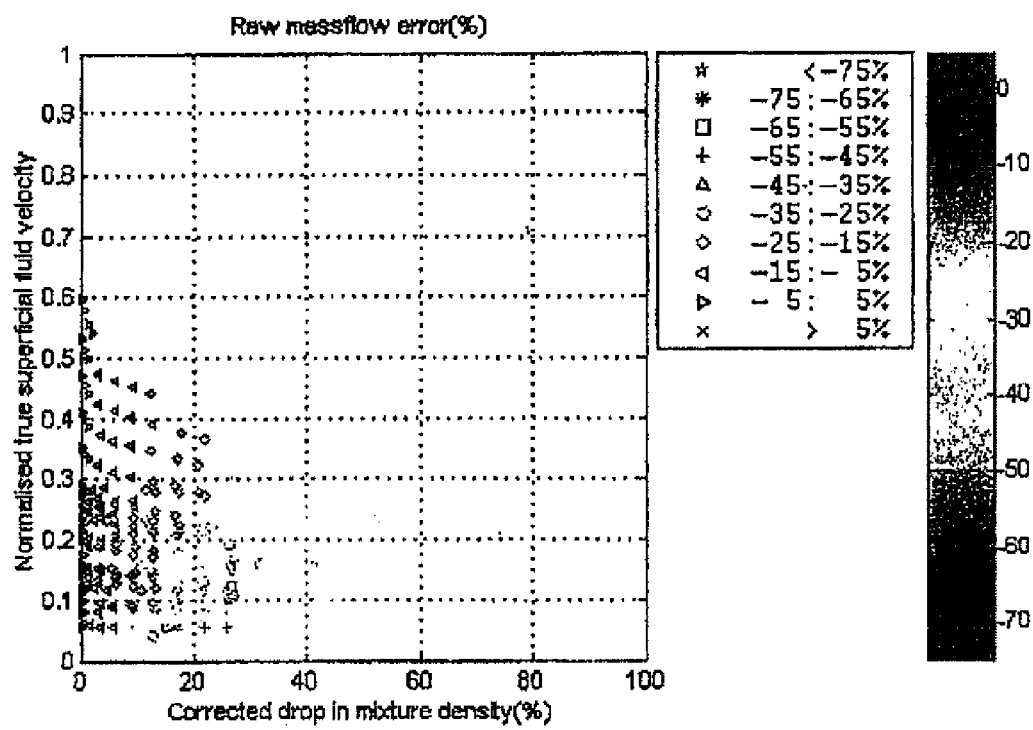

FIGS. 15A and 15B illustrate apparent mass flow errors for the data used to fit the model versus corrected drop in mixture density $\Delta\rho_{true}$ and normalized true superficial fluid velocity; i.e., the apparent mass flow error curves per flowline, together with a scatter plot of the apparent mass flow error versus corrected drop in density $\Delta\rho_{true}$ and normalized true superficial fluid velocity $v_{tn}$, as shown in Eq. 26:

$$v_{tn} = \frac{v_t}{v_{max}}, \quad v_t = \frac{m_t}{\rho_{liquid} \cdot A_T} \quad \text{Eq. 26}$$

where $m_t$ is the true fluid mass flow, i.e. the value of the mass flow independently measured, $\rho_{liquid}$ is the liquid density, $A_T$ is the flowtube cross-section area, and $v_{max}$ is the maximum value for the superficial fluid velocity (here considered 12), so that $v_{tn}$ gives the ratio of the true superficial fluid velocity from the whole range of the flowtube 215. In these examples, both drop in mixture density and superficial fluid velocity are normalized between 0 and 1 prior to fitting the model, for the purpose of ensuring numerical stability for the model optimization algorithm.

Figure 16:
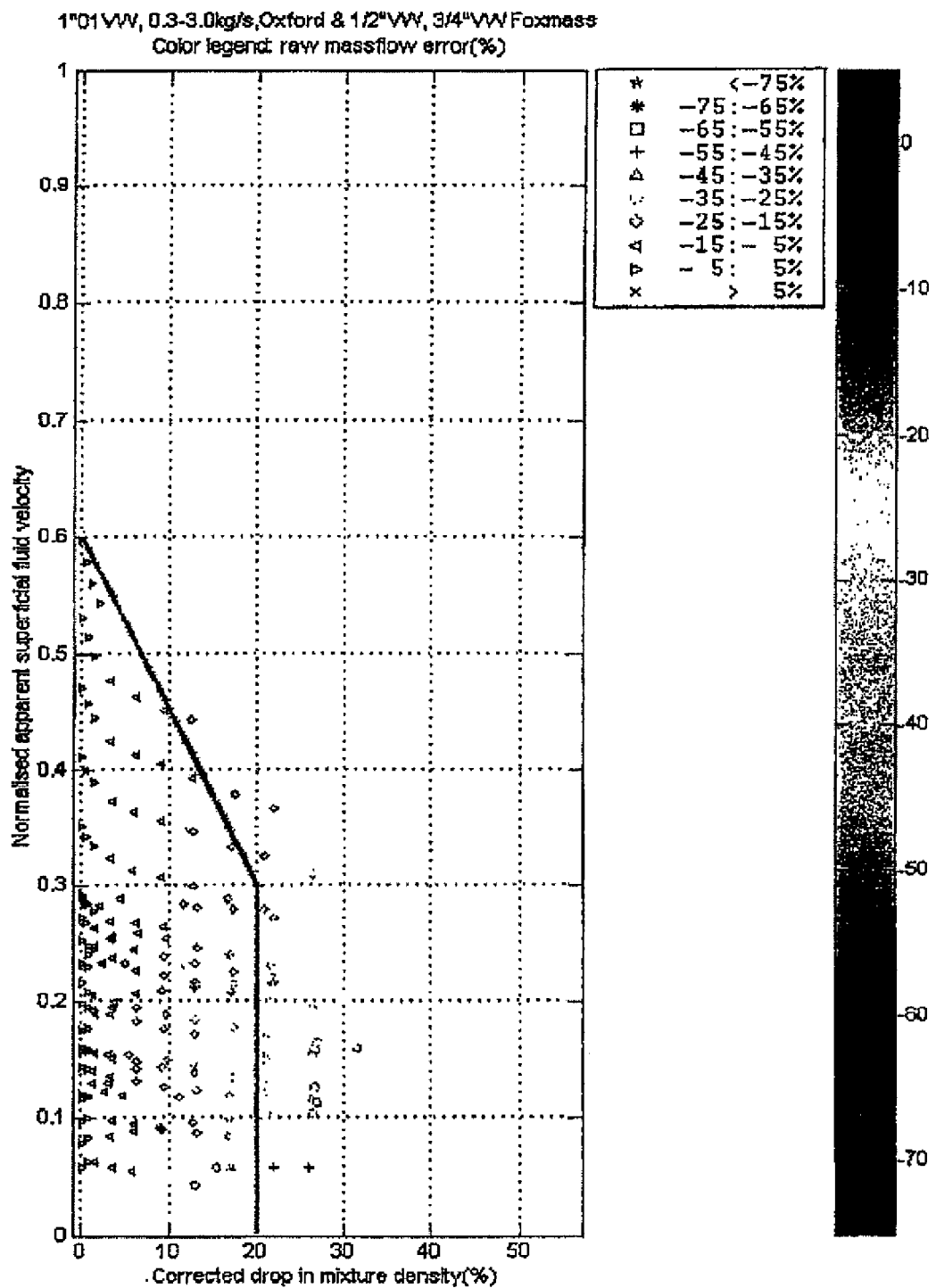

FIG. 16 illustrates apparent mass flow errors versus corrected drop in mixture density and normalized apparent superficial fluid velocity, with safety bounds for the correction mode. That is, FIG. 16 gives the scatter plot of the apparent mass flow errors versus corrected drop in density and, this time, normalized apparent superficial fluid velocity $$v_n = \frac{v}{v_{max}} = \frac{m}{v_{max} \cdot \rho \cdot A},$$

where m is the apparent fluid mass flow (i.e. as measured by the transmitter 104). Superimposed on the plot are the boundaries defining the safe region for the model, i.e., the region for which the model is expected to give an accuracy similar with the one for the fit data. Using this nomenclature, the apparent mass flow error e is given by $$e = 100 \cdot \frac{m - m_t}{m_t}.$$

The model formula for this situation is shown as Eq. 27:

$$e_n = a_1 dd_{cn} \cdot e^{a_2 dd_{cn}^2 + a_3 dd_{cn} + a_4 v_n^2 + a_5 v_n} + a_6 dd_{cn}^2 + a_7 dd_{cn} + a_8 v_n^2 a_9 v_n \quad \text{Eq. 27}$$

where $$e_n = \frac{e}{100} = \frac{m - m_t}{m_t} \quad \text{Eq. 28}$$

where, in Eqs. 27 and 28, $dd_{cn}$ is the normalized corrected drop in mixture density, and $v_n$ is the normalized apparent superficial velocity of the liquid.

In this case, the coefficient are: $a_1$=−4.78998578570465, $a_2$=4.20395000016874, $a_3$=−5.93683498873342, $a_4$=12.03484566235777, $a_5$=−7.70049487145105, $a_6$=0.69537907794202, $a_7$=−0.52153213037389, $a_8$=0.36423791515369, and $a_9$=−0.16674339233364

Figure 17:
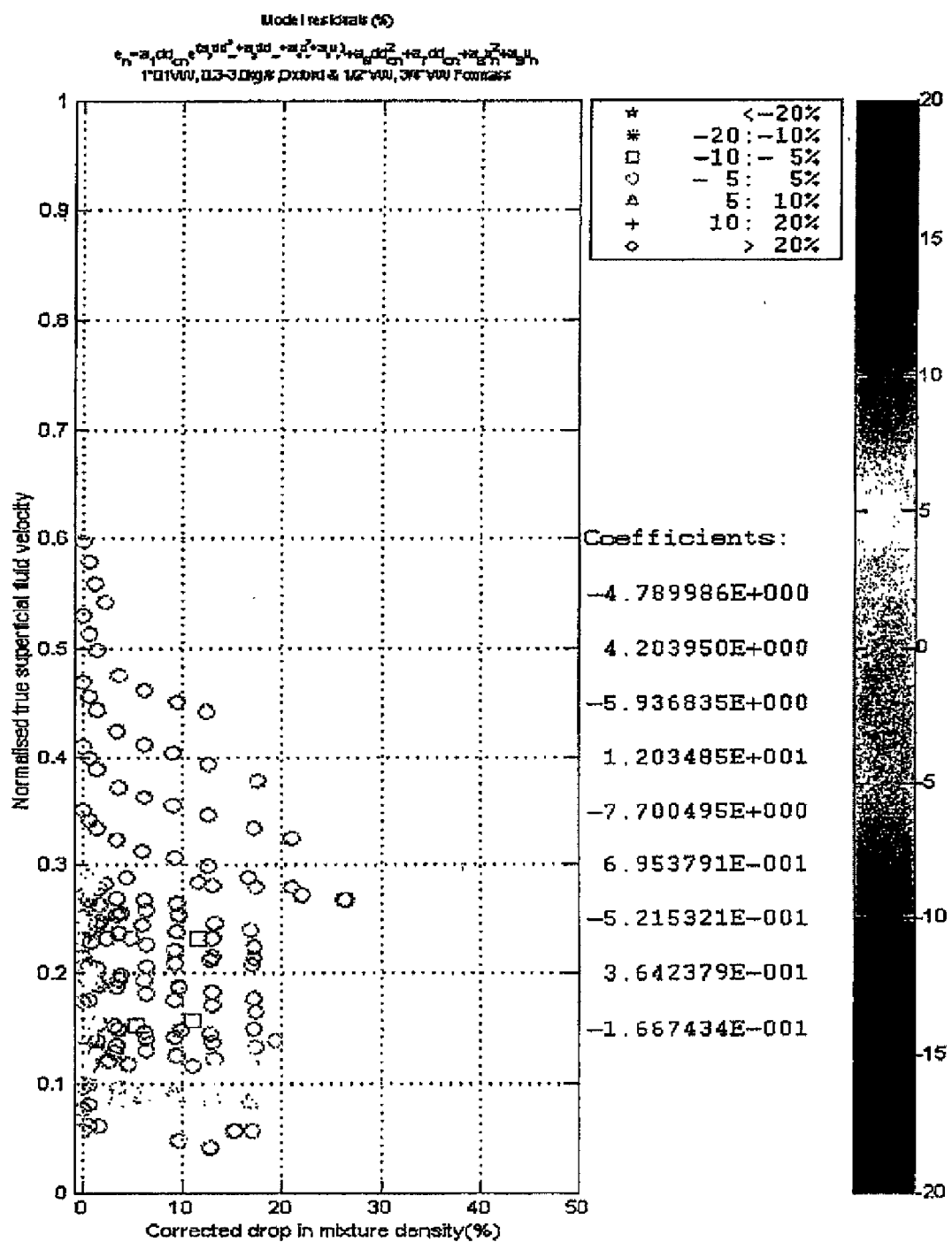
Figure 18A:
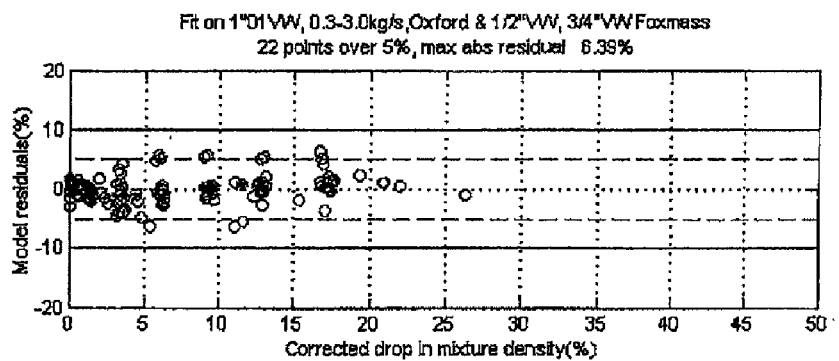
Figure 18B:
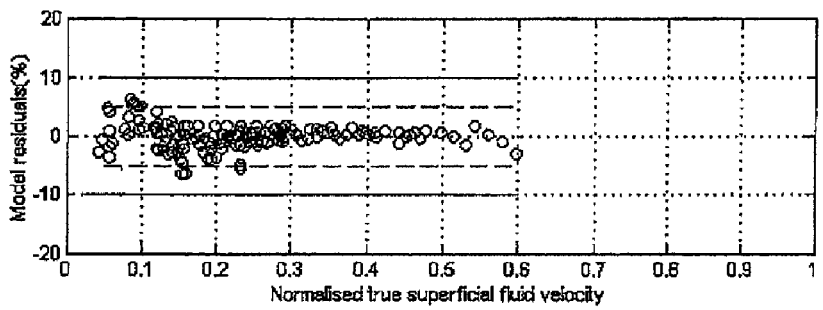
Figure 18C:
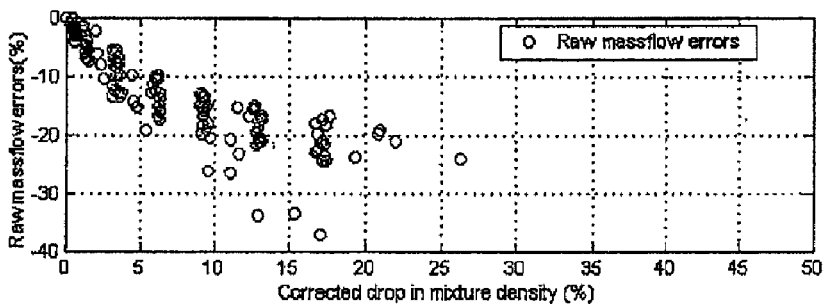
Figure 18D:
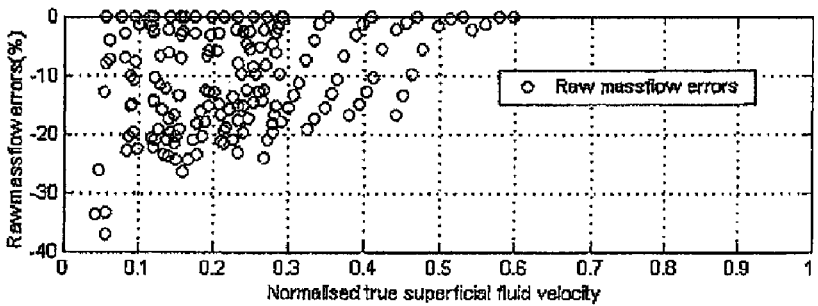
Figure 19A:
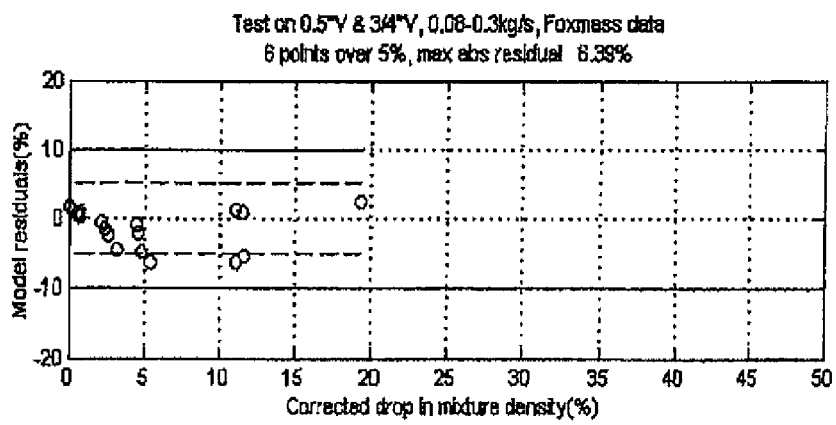
Figure 19B:
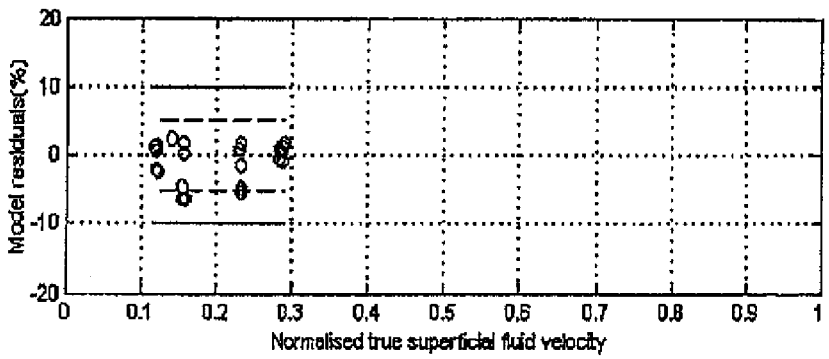
Figure 19C:
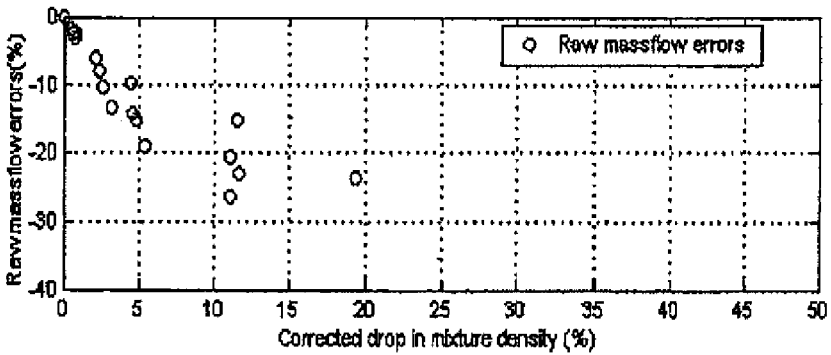
Figure 19D:
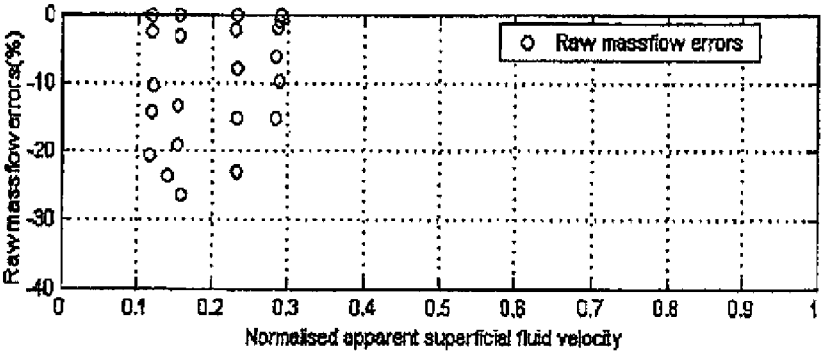
Figure 20A:
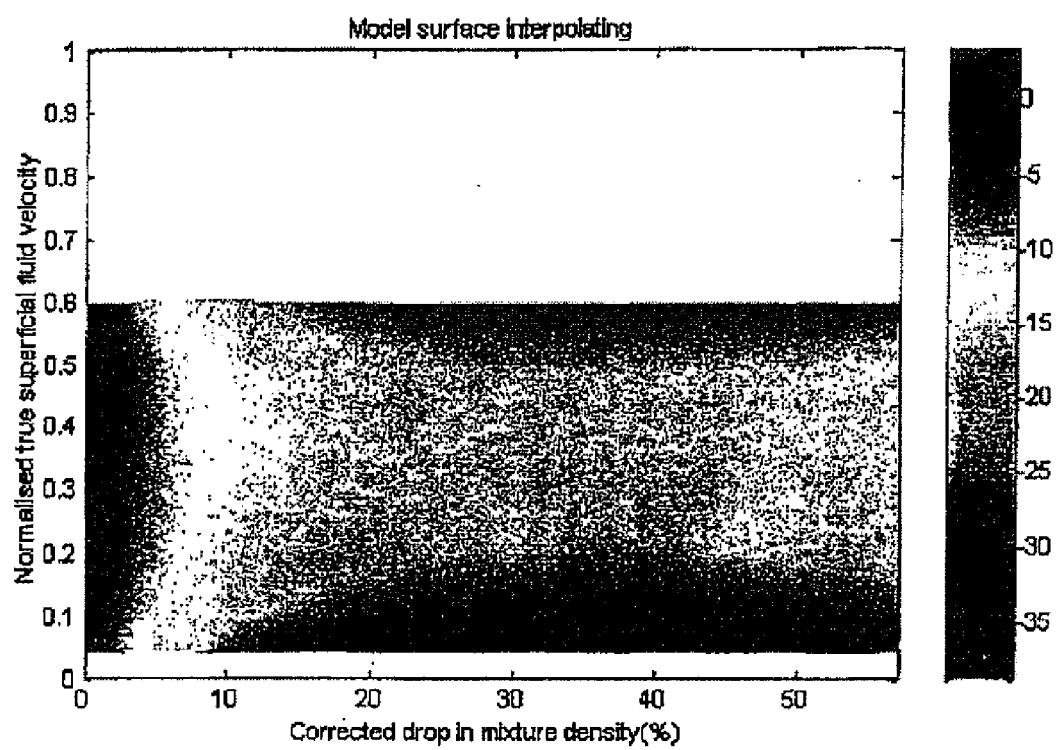
Figure 20B:
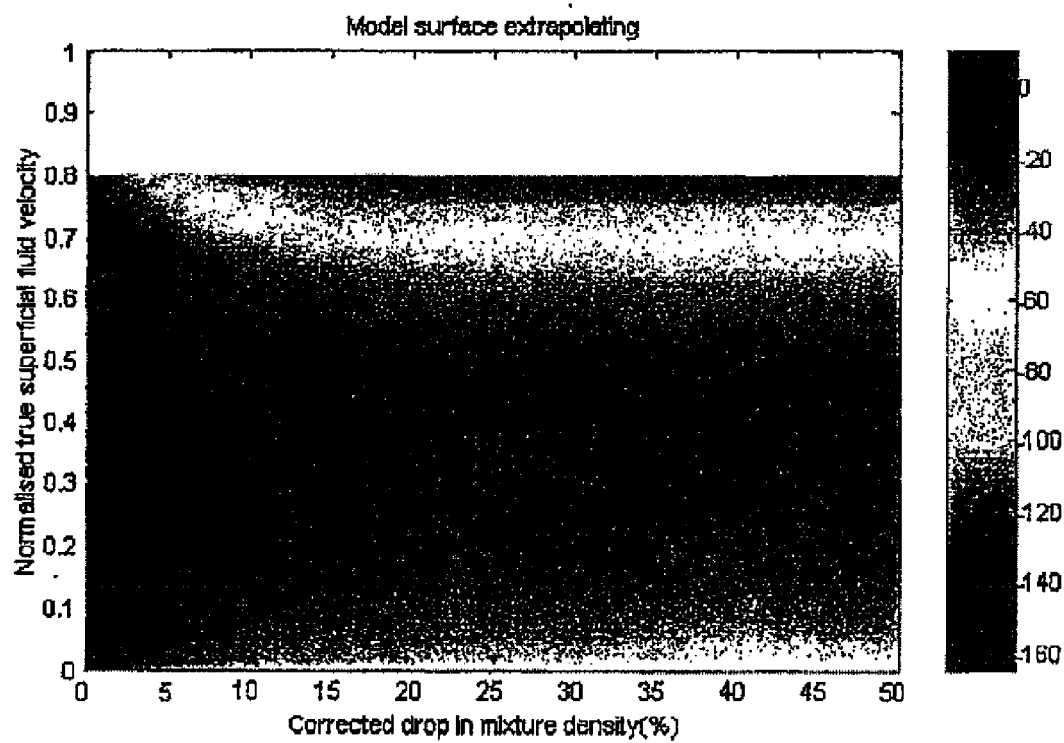

FIG. 17 illustrates a scatter plot for the model residuals, together with the model formula and coefficients; i.e., shows model residuals versus the corrected drop in mixture density and normalized true fluid velocity. FIGS. 18A-18D and FIGS. 19A-19D give the model residual errors for the whole data set used to fit the model and the actual data alone, respectively. Finally, FIGS. 20A and 20B illustrate the model surface both interpolating and extrapolating outside the safe fit area. From FIGS. 16, 20A, and 20B, the apparent mass flow (superficial liquid velocity) and drop in density bounds for the model should be understood.

To summarize, mass flow correction in the transmitter 104 is undertaken in this example by calculating an apparent drop in density, correcting it using the method(s) described above, and normalizing the resulting value by dividing it by 100 (or use the obtained normalized corrected drop in density from the density model). Then, a normalized superficial fluid velocity $v_n$ is calculated, and the model is applied to obtain an estimation of the normalized mass flow error $e_n$, where this value gives the error of the apparent mass flow as a ratio of the true mass flow. The obtained value may be un-normalized by multiplying it by 100, to thereby obtain the mass flow error as a percentage of the true mass flow. Finally, the apparent mass flow may be corrected with the un-normalized mass flow error $$m_c = \frac{m}{e_n + 1}.$$

As will be appreciated, the above description has a wide range of applications to improve the measurement and correction accuracy of a coriolis meter during two phase flow conditions. In particular, the techniques described above are particularly useful in measurement applications where the mass flow of the liquid phase and the mass flow of the gas phase must be measured and/or corrected to a high level of accuracy. One exemplary application is the measurement of the mass flow of the liquid phase and the measurement of the gas phase in oil and gas production environments.

The above discussion is provided in the context of the digital flowmeter of FIG. 2. However, it should be understood that any vibrating or oscillating densitometer or flowmeter, analog or digital, that is capable of measuring multi-phase flow that includes a gas phase of a certain percentage may be used. That is, some flowmeters are only capable of measuring process fluids that include a gas phase when that gas phase is limited to a small percentage of the overall process fluid, such as, for example, less than 5%. Other flowmeters, such as the digital flowmeter(s) referenced above, are capable of operation even when the gas void fraction reaches 40% or more.

Many of the above-given equations and calculations are described in terms of density, mass flow rate, and/or void fraction. However, it should be understood that the same or similar results may be reached using variations of these parameters. For example, instead of mass flow, a volumetric flow may be used. Additionally, instead of void fraction, liquid fraction may be used.

A number of implementations have been described. Nevertheless, it will be understood that various modifications may be made. Accordingly, other implementations are within the scope of the following claims.

What is claimed is:
1. A flowmeter comprising:
a vibratable flowtube configured to receive a flow of fluid, the fluid including a first phase and a second phase;
a driver connected to the flowtube and operable to impart motion to the flowtube;
a sensor connected to the flowtube and operable to sense the motion of the flowtube and generate a first signal;

a pressure sensor operable to sense a pressure of the fluid and generate a second signal indicating the pressure; and a controller connected to receive the first signal and the second signal, the controller being operable to determine a parameter of the first phase based on the second signal, and determine, based on the parameter and the first signal, a first flow rate of the first phase or a second flow rate of the second phase.

2. The flowmeter of claim 1 wherein the first phase includes a gas and the second phase includes a liquid.

3. The flowmeter of claim 2 wherein the parameter is a density of the gas.

4. The flowmeter of claim 3 wherein, to determine, based on the parameter and the first signal, the first flow rate of the first phase or a second flow rate of the second phase, the controller is configured to determine a gas void fraction of the fluid based on the density of the gas and to determine, based on the gas void fraction and the first signal, the first flow rate or the second flow rate.

5. The flowmeter of claim 1 wherein, to determine a first flow rate of the first phase or a second flow rate of the second phase, the controller is configured to determine the first flow rate based on the parameter and the first signal and to determine the second flow rate based on the parameter and the first signal.

6. The flowmeter of claim 1 wherein the controller is operable to input an apparent density of the fluid detected by the flowmeter and output a corrected density of the fluid.

7. The flowmeter of claim 1 wherein the parameter is a first phase fraction of the fluid that indicates an amount of the first phase in the fluid.

8. The flowmeter of claim 7 wherein the controller is operable to determine the first phase fraction using a measured temperature of the fluid.

9. The flowmeter of claim 7 wherein the controller is operable to determine the first phase fraction based on accessed characteristics of a gas present in the fluid.

10. A controller comprising:
at least one processing device; and
a storage device, the storage device storing instructions for causing the at least one processing device to:
vibrate a flowtube using a driver while a fluid is passed through the flowtube, wherein the driver is connected to the flowtube and operable to impact motion to the flowtube, the fluid including a first phase and a second phase;
receive a first signal from a sensor while the flowtube is vibrated, wherein the sensor is connected to the flowtube and is configured to sense motion of the flowtube and generate the sensor signal;
receive a second signal from a pressure sensor operable to sense a pressure of the fluid;
determine a parameter of the first phase based on the second signal; and
determine, based on the parameter and the first signal, a first flow rate of the first phase or a second flow rate of the second phase.

11. The controller of claim 10 wherein the first phase includes a gas and the second phase includes a liquid.

12. The controller of claim 11 wherein the parameter is a density of the gas.

13. The controller of claim 12 wherein the instructions for causing the at least one processing device to determine, based on the parameter and the first signal, the first flow rate of the first phase or a second flow rate of the second phase comprise instructions for causing the at least one processing device to determine a gas void fraction of the fluid based on the density of the gas and to determine, based on the gas void fraction and the first signal, the first flow rate or the second flow rate.

14. The controller of claim 10 wherein the instructions for causing the at least one processing device to determine a first flow rate of the first phase or a second flow rate of the second phase comprise instructions for causing the at least one processing device to determine the first flow rate based on the parameter and the first signal and to determine the second flow rate based on the parameter and the first signal.

15. The controller of claim 10 wherein the instructions include instructions for causing the at least one processing device to input an apparent density of the fluid and output a corrected density of the fluid.

16. The controller of claim 10 wherein the parameter is a first phase fraction of the fluid that indicates an amount of the first phase in the fluid.

17. The controller of claim 16 wherein the instructions include instructions for causing the at least one processing device to determine the first phase fraction using a measured temperature of the fluid.

18. The controller of claim 16 wherein the instructions include instructions for causing the at least one processing device to determine the first phase fraction based on accessed characteristics of a gas present in the fluid.

19. A method comprising:
determining a bulk density of a two-phase flow through a flowtube, the two-phase flow including a first phase and a second phase;
determining a density of the first phase using a measured pressure of the two-phase flow; and
determining a first mass flow rate of the first phase, based on the bulk density and the density of the first phase.

20. The method of claim 19 wherein the first phase includes a gas and the second phase includes a liquid.

21. The method of claim 19 further comprising determining a gas void fraction of the two-phase flow.

22. The method of claim 21 wherein determining a first mass flow rate of the first phase is further based on the gas void fraction.

23. The method of claim 19 wherein determining a bulk density of a two-phase flow comprises determining a corrected bulk density from an apparent bulk density.

24. The method of claim 19 wherein determining a density of the first phase comprises determining a density of the first phase using a measured temperature of the two-phased flow.

* * * * *